US012612610B2

(12) United States Patent
Hodgkinson et al.

(10) Patent No.: US 12,612,610 B2
(45) Date of Patent: Apr. 28, 2026

(54) COMPOSITIONS AND METHODS FOR CONTROLLING BLOOD PRESSURE

(71) Applicant: Duke University, Durham, NC (US)

(72) Inventors: Conrad P. Hodgkinson, Durham, NC (US); Hualing Sun, Durham, NC (US); Richard Pratt, Sandwich, MA (US); Victor J. Dzau, Durham, NC (US)

(73) Assignee: Duke University, Durham, NC (US)

( * ) Notice: Subject to any disclaimer, the term of this patent is extended or adjusted under 35 U.S.C. 154(b) by 646 days.

(21) Appl. No.: 18/054,745

(22) Filed: Nov. 11, 2022

(65) Prior Publication Data

US 2023/0313160 A1 Oct. 5, 2023

Related U.S. Application Data

(63) Continuation of application No. PCT/US2021/031963, filed on May 12, 2021.

(60) Provisional application No. 63/122,626, filed on Dec. 8, 2020, provisional application No. 63/023,278, filed on May 12, 2020.

(51) Int. Cl.
| | |
|---|---|
| *C12N 9/22* | (2006.01) |
| *A61P 9/12* | (2006.01) |
| *C12N 15/86* | (2006.01) |

(52) U.S. Cl.
CPC ................. *C12N 9/22* (2013.01); *A61P 9/12* (2018.01); *C12N 15/86* (2013.01); *C12N 2310/20* (2017.05); *C12N 2750/14143* (2013.01)

(58) Field of Classification Search
CPC .............. C12N 15/113; C12N 2310/11; C12N 2310/3515; C12N 2320/32; C12N 2310/20; C12N 2750/14143; C12N 2800/40; C12N 15/86; C12N 9/22; C12N 15/907; C12N 2310/14; A61P 9/12
USPC ..................... 435/6.1, 91.1, 91.31, 455, 458; 514/44 A, 44 R; 536/23.1, 24.5
See application file for complete search history.

(56) References Cited

U.S. PATENT DOCUMENTS

| | | | |
|---|---|---|---|
| 5,846,946 A | 12/1998 | Huebner et al. | |
| 8,404,658 B2 | 3/2013 | Hajar et al. | |
| 8,454,972 B2 | 6/2013 | Nabel et al. | |
| 2015/0232883 A1 | 8/2015 | Dahlman et al. | |
| 2018/0320163 A1 | 11/2018 | Koonin et al. | |
| 2019/0256900 A1 | 8/2019 | Zhang et al. | |
| 2020/0199555 A1* | 6/2020 | Zhang ................. | C12N 15/907 |
| 2024/0191236 A1* | 6/2024 | Foster ................. | C12N 15/113 |

FOREIGN PATENT DOCUMENTS

| | | |
|---|---|---|
| WO | 9324640 A2 | 12/1993 |
| WO | 2017/165688 A1 | 9/2017 |
| WO | 2019222166 A1 | 11/2019 |

OTHER PUBLICATIONS

Wang et al (Nature Reviews, vol. 18, pp. 358-378 (2019)) (Year: 2019).*
European Patent Office, Extended European Search Report for European Application No. 21803845.3 dated Jun. 3, 2024, 7 pages.
Altschul, S., et al., "Gapped BLAST and PSI-BLAST: a new generation of protein database search programs," Nucleic Acids Research, 1997, vol. 25, No. 17, pp. 3389-3402.
Altschul, S., et al., "Basic local alignment search tool," Journal of Molecular Biology, 1990, vol. 215, Issue 3, pp. 403-410.
Henikoff, S., et al., "Amino acid substitution matrices from protein blocks," Proc. Natl. Acad. Sci. USA 1992, vol. 89, pp. 10915-10919.
Kyte, J., et al., "A simple method for displaying the hydropathic character of a protein," J. Mol. Biol. 1982, pp. 105-132.
International Search Report and Written Opinion for International Application No. PCT/US2021/031963, mailed Sep. 17, 2021, 14 pages.
International Preliminary Report on Patentability for International Application No. PCT/US2021/031963, mailed Nov. 24, 2022, 10 pages.
Liu, C., et al., "Delivery strategies of the CRISPR-Cas9 gene-editing system for therapeutic applications," Journal of Controlled Release 2017, vol. 266, pp. 17-26.
Needleman, S., et al., "A general method applicable to the search for similarities in the amino acid sequence of two proteins," Journal of Molecular Biology 1970, vol. 48, Issue 3, pp. 443-453.
Niu, Y., et al., "Generation of gene-modified cynomolgus monkey via Cas9/RNA-mediated gene targeting in one-cell embryos," Cell 2014, vol. 156(4), pp. 836-843.
Pearson, W., et al., "Improved tools for biological sequence comparison," Proc. Natl. Acad Sci. USA 1988, vol. 85, pp. 2444-2448.
Ran, F., et al., "Genome engineering using the CRISPR-Cas9 system," Nature Protocols 2013, vol. 8, pp. 2281-2308.
Smith, T., et al., "Comparison of Biosequences," Advances in Applied Mathematics 1981, vol. 2, pp. 482-489.
Sun, H., et al., "CRISPR/Cas9 Mediated Deletion of the Angiotensinogen Gene Reduces Hypertension: A Potential for Cure?" Hypertension, 2021, vol. 77, pp. 1990-2000.
Zuris, J., et al., "Cationic lipid-mediated delivery of proteins enables efficient protein-based genome editing in vitro and in vivo," Nature Biotechnology 2015, vol. 33, pp. 73-80.

* cited by examiner

*Primary Examiner* — Jane J Zara

(74) *Attorney, Agent, or Firm* — Nutter McClennen & Fish LLP

(57) ABSTRACT

The present disclosure describes compositions and methods for treating hypertension in a subject.

18 Claims, 19 Drawing Sheets

Specification includes a Sequence Listing.

COMPOSITIONS AND METHODS FOR CONTROLLING BLOOD PRESSURE

CROSS-REFERENCE TO RELATED APPLICATIONS

This application is a continuation of International Patent Application No. PCT/US2021/031963, filed May 12, 2021, which claims the benefit of priority under 35 U.S.C. 119(e) to U.S. Provisional Patent Application No. 63/023,278, filed May 12, 2020, and U.S. Provisional Patent Application No. 63/122,626, filed Dec. 8, 2020, the entire disclosure of which is incorporated herein by reference.

SEQUENCE LISTING

This application contains a Sequence Listing which has been submitted as a WIPO Standard ST.26 XML file via Patent Center. Said XML file, created on Nov. 11, 2022, is entitled "123658-10603.xml" and is 40,695 bytes in size. The sequence listing is incorporated herein by reference.

BACKGROUND

Hypertension affects more than one billion people worldwide. High blood pressure negatively affects the heart; inducing left ventricular hypertrophy and systolic/diastolic dysfunction. Untreated, this can lead to heart failure. Despite the development of a number on antihypertensive therapies, the number of people with uncontrolled hypertension continues to rise. The current treatment regime for hypertension is an ACE inhibitor in combination with a calcium antagonist or a diuretic. While effective, this treatment regime can induce a number of side-effects including hyperkalaemia, renal impairment, cough, skin rashes, loss of taste, and angioneurotic oedema. Consequently, there has been much interest in developing new ways of treating hypertension. A major focus for the development of novel therapies has been siRNA mediated silencing of genes involved in hypertension. Initial studies with direct injection of siRNAs were moderately successful; reducing systolic blood pressure by ~25 mmHg. While encouraging, injected siRNAs are rapidly degraded and their effects on blood pressure are short-lived. Repeated siRNA injections would be clinically invasive; therefore, researchers developed viral based methods to ensure prolonged siRNA expression. Due to their non-integrating nature, AAVs have been the preferred choice for siRNA expression. To date, a single injection of AAVs carrying siRNAs that target Angiotensinogen; D 1 Adrenergic receptor; Angiotensinogen-II Type-1 receptor; as well as Endothelin-1, amongst others, have all been demonstrated to significantly reduce blood pressure. Reductions in blood pressure can be prolonged (>10 weeks); however, the need for AAV persistence to maintain siRNA expression is problematic as the AAV can be lost during cell proliferation.

SUMMARY OF INVENTION

The invention described and claimed herein provides a solution to the drawbacks of previous approaches, e.g., those described above. Accordingly, the invention provides a guide RNA (gRNA) that targets an angiotensinogen (AGT) gene, e.g., exon 2 of the AGT gene. In some embodiments, the gRNA comprises the polynucleotide sequence of guide RNA to target human AGT gene comprises CCTTC-CACCTCGTCATCCACA (human gRNA1; SEQ ID NO:1), TCATTGTGGATGACGAGGTGG (human gRNA2; SEQ ID NO:2), or GATATTTCAGGGTATGCGGAA (human gRNA3; SEQ ID NO:3). For example, the target AGT gene comprises an Angiotensinogen (AGT)-II gene (AGT-II). An exemplary composition comprising the gRNA described above further comprises a hepatocyte-tropic vector and/or promoter, e.g., for preferential delivery to liver cells (hepatocytes), which cell type is a major source of AGT in the human body. For example, the vector comprises adeno-associated virus-8 (AAV-8), which is characterized by a tropism for hepatocytes.

AGT is also made by cells of the heart, central nervous system such as neuronal cells or cells of brain tissue, as well as kidney cells. Thus, a gRNA composition may further comprise a heart-tropic vector, a neuronal cell-tropic vector, or a kidney-tropic vector. For example, the heart-tropic vector comprises AAV-1 or AAV-9, the neuronal cell-tropic vector comprises AAV-1, AAV-4, AAV-5, or AAV-6, and the kidney-tropic vector comprises AAV-2 or AAV-DJ. AGT is also produces by other cells of the cardio vascular system, e.g., blood vessel cells such as cells of blood vessel walls.

A gRNA composition may also further comprise a CRISPR/Cas system component. For example, the CRISPR/Cas system component comprises at least a Cas9 nuclease.

Also within the invention is a method of treating or controlling high blood pressure in a mammalian subject. An exemplary method of treating a subject suffering from hypertension or prehypertension comprises administering to the subject a composition comprising a guide RNA (gRNA) that targets an angiotensinogen (AGT) gene, the gRNA comprising the polynucleotide sequence of CCTTC-CACCTCGTCATCCACA (human gRNA1; SEQ ID NO:1); TCATTGTGGATGACGAGGTGG (human gRNA2; SEQ ID NO:2), or GATATTTCAGGGTATGCGGAA (human gRNA3; SEQ ID NO:3) and a hepatocyte-tropic, heart-tropic vector, a neuronal cell-tropic vector, or a kidney-tropic vector.

Hypertension, also known as high or raised blood pressure, is a condition in which the blood vessels have persistently raised pressure. Hypertension is diagnosed if, when it is measured on two different days, the systolic blood pressure readings on both days is ≥140 mm mercury (Hg) and/or the diastolic blood pressure readings on both days is ≥90 mm Hg. Prehypertension is when blood pressure values are above normal or optimal levels. The World Health Organization classifies prehypertension as a blood pressure reading that measures between 120/80 and 139/89.

As described above, an exemplary therapeutic method utilizes a hepatocyte-tropic vector such as AAV-8; a heart-tropic vector such as AAV-1 or AAV-9; a neuronal cell- or brain-tropic vector such as AAV-1, AAV-4, AAV-5, or AAV-6; and/or a kidney-tropic vector such as AAV-2 or AAV-DJ.

The product of the AGT gene is the Angiotensin protein. Angiotensin is cleaved by Renin to make Angiotensin-I (AGt-I). Angiotensin-I is further cleaved by ACE to make Angiotensin-II (AGT-II)

The AGT gene is deleted in a cell comprising the administered composition; thus, in treated cells, no AGT gene product is made. In treated cells or tissues, the expression of the AGT gene is absent or reduced compared to an untreated cell or tissue. An exemplary reduction in gene expression is at least 25% 50%, 75%, 2-fold, 5-fold, 10-fold or more compared to an untreated cell or tissue.

The composition to be administered for treatment further comprises a CRISPR/Cas system component, wherein the component comprises at least a Cas9 nuclease. Cas9 Nuclease, *S. pyogenes*, is an RNA-guided endonuclease that catalyzes site-specific cleavage of double stranded DNA.

The disclosure relates to modifying a gene sequence using a CRISPR-Cas9 or other nucleic acid editing system, and methods and delivery systems for achieving such gene modification, such as viral or non-viral delivery systems. In embodiments, the nucleic acid editing system is CRISPR-Cas system such as Cas9 nuclease. Alternative nucleases include meganucleases, zinc finger nucleases (ZFNs), and transcription activator-like effector-based nucleases (TALEN).

The therapy described above leads to systolic and/or diastolic blood pressure being reduced by at least 10 millimeters of mercury (mm Hg). For example, systolic and/or diastolic blood pressure is reduced by 20-30 points (mm Hg). The composition is administered is administered to the body in a variety of routes, e.g., the composition is administered intravenously. Cells or tissues may also be treated ex vivo. In an example, the composition is administered to a human subject at a dose of about $1\text{-}2\times10^{15}$ genome copies of AAV per 60 kg.

The method is an efficient therapy for hypertension/prehypertension, e.g., the composition is administered once in the subject life time and confers clinical benefit with one or few treatments. In other examples, the composition is administered annually or is administered every 2-5 years, or as needed to maintain healthy blood pressure.

The treatment affects somatic cells. Germ line cells are not affected by the treatment. For example, the treatment is administered to individuals 35 years old or older (and have been diagnosed with hypertension or prehypertension). The method is an efficient therapy for prehypertension (systolic BP (SBP) 120 to 139 or diastolic BP (DBP) 80 to 89 mm Hg) and hypertension (>140/90 mm Hg). The treatment only affects somatic cells. Gene-editing does not occur in germ line cells and cannot be inherited. In contrast to conventional therapies, which require multiple and frequent dosing, this method/composition is administered once. A single dose is sufficient for lifelong control of blood pressure.

The invention also encompasses a DNA targeting composition or vector comprising an endonuclease and at least one gRNAs described above as well as a kit that includes a DNA targeting composition or vector comprising an endonuclease and at least one gRNA (as described above) as well as instructions for use to reduce blood pressure in a mammalian subject.

The Summary is provided to introduce a selection of concepts that are further described below in the Detailed Description. This Summary is not intended to identify key or essential features of the claimed subject matter, nor is it intended to be used as an aid in limiting the scope of the claimed subject matter.

The present disclosure is based, in part, on the findings by the inventors of the effects of targeting the Crispr-Cas9 system to the machinery that directly regulates blood pressure; namely the Renin-Angiotensin-Aldosterone (RAAS) system. Results of experiments by the inventors showed effective Crispr-Cas9 targeting of Angiotensinogen (AGT) in vitro. In vivo, effective Crispr-Cas9 targeting of an Angiotensinogen (AGT) gene (e.g., Angiotensinogen-II) in liver hepatocytes was associated with significant reductions of blood pressure in art-recognized rat models of hypertension. Further, the inventors observed reduced blood pressure in normotensive rats and that Crispr-Cas9 targeting of the liver Angiotensinogen (AGT) gene prevented low salt induced hypertension. Importantly, the effects on blood pressure were sustained and prolonged.

Accordingly, one aspect of the present disclosure provides a guide RNA (gRNA) that targets an angiotensinogen (AGT)

gene and comprising, consisting of, or consisting essentially of a polynucleotide sequence corresponding to at least one of SEQ ID NO: numbers described in Tables 1A, 1B, or 1B below.

Another aspect of the present disclosure provides a DNA targeting composition comprising an endonuclease and at least one gRNA as provided herein.

Another aspect of the present disclosure provides a vector comprising, consisting of, or consisting essentially of at least one gRNA as provided herein and at least one endonuclease. In some embodiments, the vector comprises a viral vector. In one embodiment, the vector comprises an Adeno-associated virus (AAV) vector. In certain embodiments, the vector comprises an AAV-8 vector.

In another embodiment, the vector comprises at least one tissue-specific promoter operably linked to the polynucleotide sequence encoding at least one of the gRNA sequences or endonuclease as provided herein. In some embodiments, the tissue-specific promoter comprises a hepatocyte-specific promoter.

Another aspect of the present provides a cell comprising, consisting of, or consisting essentially of at least at least one gRNA and/or a polynucleotide sequence encoding the same as provided herein, a composition as provided herein, or a vector as provided herein.

Another aspect of the present disclosure provides a kit comprising, consisting of, or consisting essentially of cell comprising the cell comprising at least one gRNA and/or a polynucleotide sequence encoding the same as provided herein, a composition as provided herein or a vector as provided herein, and instructions for use.

Another aspect of the present disclosure provides a modified adeno-associated viral vector for deleting and/or gene editing an Angiotensinogen (AGT) gene comprising, consisting of, or consisting essentially at least one polynucleotide sequence encoding a gRNA as provided herein and an endonuclease.

Another aspect of the present disclosure provides a method of deleting an Angiotensinogen (AGT) gene comprising, consisting of, or consisting essentially of administering to a cell at least one gRNA as provided herein, a polynucleotide sequence encoding the DNA composition as provided herein, the vector as provided herein, the composition as provided herein, or the modified adeno-associated viral vector provided herein.

Another aspect of the present disclosure provides a method of treating a subject suffering from hypertension comprising, consisting of, or consisting essentially of administering to the subject at least one gRNA as provided herein, a polynucleotide sequence encoding the DNA composition as provided herein, the vector as provided herein, the composition as provided herein, or the modified adeno-associated viral vector provided herein.

Another aspect of the present disclosure provides a method of treating a subject suffering from high blood pressure in a subject comprising, consisting of, or consisting essentially of administering to the subject at least one gRNA as provided herein, a polynucleotide sequence encoding the DNA composition as provided herein, the vector as provided herein, the composition as provided herein, or the modified adeno-associated viral vector provided herein.

In some embodiments, a subject is a mammal. In certain embodiments, the mammal is a rodent (e.g., a mouse or a rat), a primate (e.g., a chimpanzee, a gorilla, a monkey, a gibbon, a baboon), a cow, a camel, a dog, a cat, a horse, a llama, a sheep, a goat, or a pig. In preferred embodiments, the subject is a human.

Although drugs exist to treat hypertension, those treatments have poor compliance, are short-lived, and are expensive. The compositions and methods of the invention overcome those drawbacks in that they do not rely on patient compliance, the treatment is long-lived (effective with only one treatment), and are cost-effective (one or few treatments).

Each embodiment disclosed herein is contemplated as being applicable to each of the other disclosed embodiments. Thus, all combinations of the various elements described herein are within the scope of the invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

The accompanying Figures and Examples are provided by way of illustration and not by way of limitation. The foregoing aspects and other features of the disclosure are explained in the following description, taken in connection with the accompanying example figures (also "FIG.") relating to one or more embodiments, in which:

FIGS. 1A-E show the development of Crispr-Cas9 system for targeting the liver Angiotensinogen-II (AGT) gene in accordance with an embodiment of the present disclosure.

(FIG. 2B) Adult SHR; and (FIG. 2C) Adult SD rats. One week after injection, blood was removed and plasma analyzed for AGT levels by ELISA. N=5 per group. **P<0.01.

FIGS. 3A-B show that AAV8-Cas9-AGT gRNA reduces blood pressure in the spontaneously hypertensive rat in accordance with an embodiment of the present disclosure.

FIGS. 5A-I illustrate the development of Crispr-Cas9 system for targeting the liver Angiotensinogen-II (AGT) gene.

(FIG. 9C) Angiotensinogen-I levels; (FIG. 9D) Angiotensinogen-II levels; as well as (FIG. 9FE) Renin activities. N=5 per group. Comparisons were made to standard chow immediately prior to the low salt diet plus furosemide regimen for each group (control and AGT gene-edited SHR): ns, not significant, *P<0.05, P<0.01, *P<0.001. The mean of the control and gene-edited groups is shown by the solid and dashed line respectively. These data indicate that AGT gene editing does not affect dietary induced changes in blood pressure in hypertensive SHR. AAV8-Cas9 (control) or AAV8-Cas9-AGTgRNA (gene-editing) viral particles ($2\times10^{12}$ viral particles) were injected into the tail vein of adult (12-week old) male SHR. After 28 days on a standard diet, the animals were placed on a low salt diet plus furosemide (Low Na+F) regimen. The animals were maintained on the low salt diet furosemide (Low Na+F) regimen for 10 days and then returned to a standard diet for a further 10 days.

DETAILED DESCRIPTION OF INVENTION

Figure 1A:
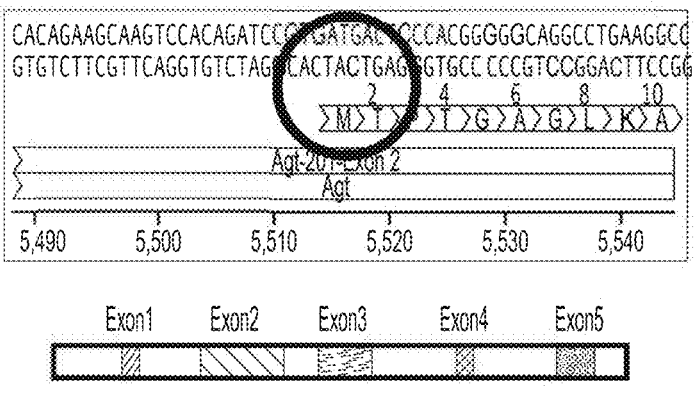
FIG. 1A is a diagram showing guide (g)-RNAs were designed to target exon 2 of the AGT gene.

Crispr-Cas9 mediated deletion of the Angiotensinogen gene reduces hypertension and represents a cure for high blood pressure. In contrast to pharmacological and siRNA-based approaches, the gene ablation strategy described herein provides a single dose treatment (or multiple dose) treatment for hypertension. For a therapeutic modality, gene ablation has to be efficient, reliable and precise. The necessary efficiency, reliability and precision is found with the Crispr-Cas9 gene editing system. Despite its' noted advantages, the Crispr-Cas9 system has had limited application in hypertension research. To date, the Crispr-Cas9 system has been used to investigate the effect of single nucleotide polymorphisms on hypertension; as well as novel genes that induce hypertension following their ablation. Several studies have demonstrated that the Crispr-Cas9 system can be used to lower blood pressure. Crispr-Cas9 mediated knockout of CPI-17 reduces blood pressure by interfering with blood vessel contraction. Similarly, blood pressure is significantly reduced following Crispr-Cas9 mediated knockout of Gper (G-protein coupled estrogen receptor). Rather than directly controlling blood pressure, Gper was found to function by modulating the gut microbiome.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result. For example, "about" about is within 10 percent of a numerical range or amount.

The use herein of the terms "including," "comprising," or "having," and variations thereof, is meant to encompass the elements listed thereafter and equivalents thereof as well as additional elements. As used herein, "and/or" refers to and encompasses any and all possible combinations of one or more of the associated listed items, as well as the lack of combinations where interpreted in the alternative ("or").

As used herein, the transitional phrase "consisting essentially of" (and grammatical variants) is to be interpreted as encompassing the recited materials or steps "and those that do not materially affect the basic and novel characteristic(s)" of the claimed invention. Thus, the term "consisting essentially of" as used herein should not be interpreted as equivalent to "comprising."

Moreover, the present disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

As used herein, the term "Adeno-associated virus" or "AAV" is used interchangeably herein refers to a small virus belonging to the genus Dependovirus of the Parvoviridae family that infects humans and some other primate species. AAV is not currently known to cause disease and consequently the virus causes a very mild immune response.

"Binding region" as used herein refers to the region within a nuclease target region that is recognized and bound by the nuclease.

Coding sequence" or "encoding nucleic acid" as used herein means the nucleic acids (RNA or DNA molecule) that comprise a polynucleotide sequence which encodes a protein. The coding sequence can further include initiation and termination signals operably linked to regulatory elements including a promoter and polyadenylation signal capable of directing expression in the cells of an individual or mammal to which the nucleic acid is administered. The coding sequence may be codon optimize.

"Complement" or "complementary" as used herein means a nucleic acid can mean Watson-Crick (e.g., A-T/U and C-G) or Hoogsteen base pairing between polynucleotides or polynucleotide analogs of nucleic acid molecules. "Complementarity" refers to a property shared between two nucleic acid sequences, such that when they are aligned antiparallel to each other, the polynucleotide bases at each position will be complementary.

"Correcting", "genome editing" and "restoring" as used herein refers to changing a mutant gene that encodes a truncated protein or no protein at all, such that a full-length functional or partially full-length functional protein expression is obtained. Correcting or restoring a mutant gene may include replacing the region of the gene that has the mutation or replacing the entire mutant gene with a copy of the gene that does not have the mutation with a repair mechanism such as homology-directed repair (HDR). Correcting or restoring a mutant gene may also include repairing a frameshift mutation that causes a premature stop codon, an aberrant splice acceptor site or an aberrant splice donor site, by generating a double stranded break in the gene that is then repaired using non-homologous end joining (HEJ). HEJ may add or delete at least one base pair during repair which may restore the proper reading frame and eliminate the premature stop codon. Correcting or restoring a mutant gene may also include disrupting an aberrant splice acceptor site or splice donor sequence. Correcting or restoring a mutant gene may also include deleting a non-essential gene segment by the simultaneous action of two nucleases on the same DNA strand in order to restore the proper reading frame by removing the DNA between the two nuclease target sites and repairing the DNA break by NHEJ.

"Donor DNA", "donor template" and "repair template" as used interchangeably herein refers to a double-stranded DNA fragment or molecule that includes at least a portion of the gene of interest. The donor DNA may encode a full-functional protein or a partially-functional protein.

"Functional" and "full-functional" as used herein describes protein that has biological activity. A "functional gene" refers to a gene transcribed to mRNA, which is translated to a functional protein.

"Genetic construct" as used herein refers to the DNA or RNA molecules that comprise a polynucleotide sequence that encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Genome editing" as used herein refers to changing a gene. Genome editing may include correcting or restoring a mutant gene. Genome editing may include knocking out a gene, such as a mutant gene or a normal gene. Genome editing may be used to treat disease or enhance muscle repair by changing the gene of interest.

"Homology-directed repair" or "HDR" as used interchangeably herein refers to a mechanism in cells to repair double strand DNA lesions when a homologous piece of DNA is present in the nucleus, mostly in G2 and S phase of the cell cycle. HDR uses a donor DNA template to guide repair and may be used to create specific sequence changes to the genome, including the targeted addition of whole genes.

As used herein, the terms "identical" or "identity" are used interchangeably and refer to two or more nucleic acids or polypeptide sequences means that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Non-homologous end joining (NHEJ) pathway" as used herein refers to a pathway that repairs double-strand breaks in DNA by directly ligating the break ends without the need for a homologous template. The template-independent re-ligation of DNA ends by NHEJ is a stochastic, error-prone repair process that introduces random micro-insertions and micro-deletions (indels) at the DNA breakpoint. This method may be used to intentionally disrupt, delete, or alter the reading frame of targeted gene sequences. NHEJ typically uses short homologous DNA sequences called micro-homologies to guide repair. These microhomologies are often present in single-stranded overhangs on the end of double-strand breaks. When the overhangs are perfectly compatible, NHEJ usually repairs the break accurately, yet imprecise repair leading to loss of polynucleotides may also occur, but is much more common when the overhangs are not compatible.

As used herein, the term "Normal gene" refers to a gene that has not undergone a change, such as a loss, gain, or exchange of genetic material. The normal gene undergoes normal gene transmission and gene expression.

"Nuclease mediated NHEJ" as used herein refers to NHEJ that is initiated after a nuclease, such as an endonuclease, cuts double stranded DNA.

As used herein, the terms "nucleic acid" or "oligonucleotide" or "polynucleotide" means at least two polynucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

As used herein, the term "operably linked" means that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

"Partially-functional" as used herein describes a protein that is encoded by a mutant gene and has less biological activity than a functional protein but more than a non-functional protein.

"Premature stop codon" or "out-of-frame stop codon" as used interchangeably herein refers to nonsense mutation in a sequence of DNA, which results in a stop codon at location not normally found in the wild-type gene. A premature stop codon may cause a protein to be truncated or shorter compared to the full-length version of the protein.

As used herein, the term "Promoter" means a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which may be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include, but are not limited to, the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter, human U6 (hU6) promoter, and CMV IE promoter.

As used herein, the term "Target gene" refers to any polynucleotide sequence encoding a known or putative gene product. The target gene may be a mutated gene involved in a genetic disease. In certain embodiments, the target gene comprises an Angiotensinogen (AGT) gene. In certain embodiments, the target is Angiotensinogen AGT-II (a.k.a., AngII; see FIG. 5A).

For example, the target gene for human therapy comprises the following nucleic acid sequence for the coding DNA and amino acid sequence for the AGT protein.

```
Human coding DNA:
                                        (SEQ ID NO: 5)
atg gctcctgccg gtgtgagcct gagggccacc atcctctgcc tcctggcctg ggctggcctg gctgcaggtg accgggtgta catacacccc ttccacctcg tcatccacaa tgagagtacc tgtgagcagc tggcaaaggc caatgccggg aagcccaaag accccacctt cataccctgct ccaattcagg ccaagacatc ccctgtggat gaaaaggccc tacaggacca gctggtgcta gtcgctgcaa aacttgacac cgaagacaag ttgagggccg caatggtcgg gatgctggcc aacttcttgg gcttccgtat atatggcatg cacagtgagc tatggggcgt ggtccatggg gccaccgtcc tctccccaac ggctgtcttt ggcaccctgg
```

-continued

```
cctctctcta tctgggagcc ttggaccaca cagctgacag gctacaggca atcctgggtg ttccttggaa ggacaagaac tgcacctccc ggctggatgc gcacaaggtc ctgtctgccc tgcaggctgt acagggcctg ctagtggccc agggcagggc tgatagccag gcccagctgc tgctgtccac ggtggtgggc gtgttcacag ccccaggcct gcacctgaag cagccgtttg tgcagggcct ggctctctat acccctgtgg tcctcccacg ctctctggac ttcacagaac tggatgttgc tgctgagaag attgacaggt tcatgcaggc tgtgacagga tggaagactg gctgctccct gatgggagcc agtgtggaca gcaccctggc tttcaacacc tacgtccact tccaagggaa gatgaagggc ttctccctgc tggccgagcc ccaggagttc tgggtggaca acagcacctc agtgtctgtt cccatgctct ctggcatggg caccttccag cactggagtg acatccagga caacttctcg gtgactcaag tgcccttcac tgagagcgcc tgcctgctgc tgatccagcc tcactatgcc tctgacctgg acaaggtgga gggtctcact ttccagcaaa actccctcaa ctggatgaag aaactatctc cccggaccat ccacctgacc atgccccaac tggtgctgca aggatcttat gacctgcagg acctgctcgc ccaggctgag ctgcccgcca ttctgcacac cgagctgaac ctgcaaaaat tgagcaatga ccgcatcagg gtggggagg tgctgaacag catttttttt gagcttgaag cggatgagag agagcccaca gagtctaccc aacagcttaa caagcctgag gtcttggagg tgaccctgaa ccgcccattc ctgtttgctg tgtatgatca aagcgccact gccctgcact tcctgggccg cgtggccaac ccgctgagca gcagcatga
```

Human amino acid sequence:

(SEQ ID NO: 6)

```
MRKRAPQSEM APAGVSLRAT ILCLLAWAGL AAGDRVYIHP

FHLVIHNEST CEQLAKANAG KPKDPTFIPA PIQAKTSPVD

EKALQDQLVL VAAKLDTEDK LRAAMVGMLA NFLGFRIYGM

HSELWGVVHG ATVLSPTAVF GTLASLYLGA LDHTADRLQA

ILGVPWKDKN CTSRLDAHKV LSALQAVQGL LVAQGRADSQ

AQLLLSTVVG VFTAPGLHLK QPFVQGLALY TPVVLPRSLD

FTELDVAAEK IDRFMQAVTG WKTGCSLMGA SVDSTLAFNT

YVHFQGKMKG FSLLAEPQEF WVDNSTSVSV PMLSGMGTFQ

HWSDIQDNFS VTQVPFTESA CLLLIQPHYA SDLDKVEGLT

FQQNSLNWMK KLSPRTIHLT MPQLVLQGSY DLQDLLAQAE

LPAILHTELN LQKLSNDRIR VGEVLNSIFF ELEADEREPT

ESTQQLNKPE VLEVTLNRPF LFAVYDQSAT ALHELGRVAN

PLSTA.
```

Rat AGT target sequences are provided below:

Rat coding DNA sequence:

(SEQ ID NO: 7)

```
atgactccca cgggggcagg cctgaaggcc accatcttct gcatcctgac ctgggtcagc ctgacagctg gggaccgcgt atacatccac ccctttcatc tcctctacta cagcaagagc acctgcgccc agctggagaa ccccagtgtg gagacgctcc cagagccaac ctttgagcct gtgcccattc aggccaagac ctcccccgtg gatgagaaga ccctgcgaga taagctcgtg ctggccactg agaagctaga ggctgaggat cggcagcgag ctgcccaggt cgcgatgatt gccaacttca tgggtttccg catgtacaag atgctgagtg aggcaagagg tgtagccagt ggggccgtcc tctctccacc ggccctcttt ggcaccctgg tctctttcta ccttggatcg ttggatccca cggccagcca gttgcaggtg ctgctgggcg tccctgtgaa ggagggagac tgcacctccc ggctggacgg acataaggtc ctcactgccc tgcaggctgt tcagggcttg ctggtcaccc agggtggaag cagcagccag acacccctgc tacagtccac cgtggtgggc ctcttcactg ccccaggctt gcgcctaaaa cagccatttg ttgagagctt gggtcccttc accccccgcca tcttccctcg ctctctggac ttatccactg acccagttct tgctgcccag aaaatcaaca ggtttgtgca ggctgtgaca gggtggaaga tgaacttgcc actagagggg gtcagcacgg acagcaccct atttttcaac acctacgttc acttccaagg gaagatgaga ggcttctccc agctgactgg gctccatgtg ttctgggtgg acaacagcac ctcagtgtct gtgcccatgc tctcgggcac tggcaacttc cagcactgga gtgacgccca gaacaacttc tccgtgacac gcgtgcccct gggtgagagt gtcaccctgc tgctgatcca gccccagtgc gcctcagatc tcgacagggt ggaggtcctc gtcttccagc acgacttcct gacttggata aagaacccgc ctcctcgggc catccgtctg accctgccgc agctggaaat tcggggatcc tacaacctgc aggacctgct ggctcaggcc aagctgtcta ccctttggg tgctgaggca aatctgggca agatgggtga caccaacccc cgagtgggag aggttctcaa cagcatcctc cttgaactcc aagcaggcga ggaggagcag cccacagagt ctgcccagca gcctggctca cccgaggtgc tggacgtgac cctgagcagt ccgttcctgt tcgccatcta cgagcgggac tcaggtgcgc tgcactttct gggcagagtg gataaccccc aaaatgtggt gtga
```

-continued

```
Rat amino acid sequence of full length protein:
                                    (SEQ ID NO: 8)
MTPTGAGLKA TIFCILTWVS LTAGDRVYIH PFHLLYYSKS

TCAQLENPSV ETLPEPTFEP VPIQAKTSPV DEKTLRDKLV

LATEKLEAED RQRAAQVAMI ANFMGFRMYK MLSEARGVAS

GAVLSPPALF GTLVSFYLGS LDPTASQLQV LLGVPVKEGD

CTSRLDGHKV LTALQAVQGL LVTQGGSSSQ TPLLQSTVVG

LFTAPGLRLK QPFVESLGPF TPAIFPRSLD LSTDPVLAAQ

KINRFVQAVT GWKMNLPLEG VSTDSTLFFN TYVHFQGKMR

GFSQLTGLHE FWVDNSTSVS VPMLSGTGNF QHWSDAQNNF

SVTRVPLGES VTLLLIQPQC ASDLDRVEVL VFQHDFLTWI

KNPPPRAIRL TLPQLEIRGS YNLQDLLAQA KLSTLLGAEA

NLGKMGDTNP RVGEVLNSIL LELQAGEEEQ PTESAQQPGS

PEVLDVTLSS PFLFAIYERD SGALHFLGRV DNPQNVV
```

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition.

As used herein, "tropism" and/or "tropic" refer to the targeting or specificity of the viral vector used to deliver gene editing components. different AAV serotype vectors have been shown to exhibit distinct tropism for various tissues and organs and recombinant AAV vectors are efficient for gene delivery to a wide variety of cell types, tissue, and organs. A specified AAV serotype preferentially binds to or delivers genetic material to a specified cell or tissue type, e.g., delivery to the specified cell or tissue type is at least 10%, 25%, 50%, 2-fold, 5-fold, 10-fold, or more compared to a cell or tissue other than the specified cell or tissue type. For example, an AAV-8 serotype vector is hepatocyte-tropic and therefore preferentially binds to/delivers genetic material to liver cells, e.g., hepatocytes. See also Table 2.

"Variant" used herein with respect to a nucleic acid means (i) a portion or fragment of a referenced polynucleotide sequence; (ii) the complement of a referenced polynucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

A "Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties {e.g., hydrophilicity, degree and distribution of charged regions) is recognized in the art as typically involving a minor change. These minor changes may be identified, in part, by considering the hydropathic index of amino acids, as understood in the art (see, e.g., Kyte et al., J. Mol. Biol. 157: 105-132 (1982)). The hydropathic index of an amino acid is based on a consideration of its hydrophobicity and charge. It is known in the art that amino acids of similar hydropathic indexes may be substituted and still retain protein function. In one aspect, amino acids having hydropathic indexes of ±2 are substituted. The hydrophilicity of amino acids may also be used to reveal substitutions that would result in proteins retaining biological function. A consideration of the hydrophilicity of amino acids in the context of a peptide permits calculation of the greatest local average hydrophilicity of that peptide. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

As sued herein, the term "Vector" means a nucleic acid sequence containing an origin of replication. A vector may be a viral vector, bacteriophage, bacterial artificial chromosome or yeast artificial chromosome. A vector may be a DNA or RNA vector. A vector may be a self-replicating extrachromosomal vector, and preferably, is a DNA plasmid. For example, the vector may encode an endonuclease and at least one gRNA, such as a gRNA comprising a polynucleotide sequence of any one of SEQ ID NOs: 1-3, or complement thereof.

The term "effective amount" or "therapeutically effective amount" refers to an amount sufficient to effect beneficial or desirable biological and/or clinical results. For example, an effective amount is an amount of therapeutic compound or composition that reduces blood pressure in a subject.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. The methods and compositions disclosed herein can be used on a sample either in vitro (for example, on isolated cells or tissues) or in vivo in a subject (i.e. living organism, such as a patient).

As used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) or polypeptide is free of the amino acid sequences or nucleic acid sequences that flank it in its naturally-occurring state. Purified also defines a degree of sterility that is safe for administration to a human subject, e.g., lacking infectious or toxic agents.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "identical" or percent "identity," in the context of two or more nucleic acids or polypeptide sequences, refer to two or more sequences or subsequences that are the same or have a specified percentage of amino acid residues or nucleotides that are the same (e.g., 50%, 55%, 60%, 65%, 70%, 75%, 80%, 85%, 90%, 91%, 92%, 93%, 94%, 95%, 96%, 97%, 98%, 99%, or more identity over a specified region, e.g., of an entire polypeptide sequence or an individual domain thereof), when compared and aligned for maximum correspondence over a comparison window, or designated region as measured using a sequence comparison algorithm or by manual alignment and visual inspection. Such sequences that are at least about 80% identical are said to be "substantially identical." In some embodiments, two sequences are 100% identical. In certain embodiments, two sequences are 100% identical over the entire length of one of the sequences (e.g., the shorter of the two sequences where the sequences have different lengths). In various embodiments, identity may refer to the complement of a test sequence. In some embodiments, the identity exists over a region that is at least about 10 to about 100, about 20 to about 75, about 30 to about 50 amino acids or nucleotides in length. In certain embodiments, the identity exists over a region that is at least about 50 amino acids in length, or more preferably over a region that is 100 to 500, 100 to 200, 150 to 200, 175 to 200, 175 to 225, 175 to 250, 200 to 225, 200 to 250 or more amino acids in length.

For sequence comparison, typically one sequence acts as a reference sequence, to which test sequences are compared. In various embodiments, when using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window" refers to a segment of any one of the number of contiguous positions (e.g., least about 10 to about 100, about 20 to about 75, about 30 to about 50, 100 to 500, 100 to 200, 150 to 200, 175 to 200, 175 to 225, 175 to 250, 200 to 225, 200 to 250) in which a sequence may be compared to a reference sequence of the same number of contiguous positions after the two sequences are optimally aligned. In various embodiments, a comparison window is the entire length of one or both of two aligned sequences. In some embodiments, two sequences being compared comprise different lengths, and the comparison window is the entire length of the longer or the shorter of the two sequences. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48.443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

In various embodiments, an algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. BLAST and BLAST 2.0 may be used, with the parameters described herein, to determine percent sequence identity for nucleic acids and proteins. Software for performing BLAST analyses is publicly available through the National Center for Biotechnology Information, as known in the art. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff& Henikoff, Proc. Natl. Acad. Sci. USA 89:10915 (1989)) alignments (B) of 50, expectation (E) of 10, M=5, N=−4, and a comparison of both strands.

Unless otherwise defined, all technical terms used herein have the same meaning as commonly understood by one of ordinary skill in the art to which this disclosure belongs.

A. CRISPR/Based Gene Editing System Genetic Constructs for Genome Editing of Angiotensinogen (AGT) Gene The present disclosure is based, in part, on the findings by the inventors of the effects of targeting the Crispr-Cas9 system to the machinery that directly regulates blood pressure; namely the Renin-Angiotensin-Aldosterone (RAAS) system. "Clustered Regularly Interspaced Short Palindromic Repeats" and "CRISPRs", as used interchangeably herein, refers to loci containing multiple short direct repeats that are found in the genomes of approximately 40% of sequenced bacteria and 90% of sequenced archaea. The CRISPR system is a microbial nuclease system involved in defense against invading phages and plasmids that provides a form of acquired immunity. The CRISPR loci in microbial hosts contain a combination of CRISPR-associated (Cas) genes as well as non-coding RNA elements capable of programming the specificity of the CRISPR-mediated nucleic acid cleavage. Short segments of foreign DNA, called spacers, are incorporated into the genome between CRISPR repeats, and serve as a 'memory' of past exposures.

Three classes of CRISPR systems (Types I, II and III effector systems) are known. The Type II effector system carries out targeted DNA double-strand break in four sequential steps, using a single effector enzyme, such as an endonuclease, to cleave dsDNA. Compared to the Type I and Type III effector systems, which require multiple distinct effectors acting as a complex, the Type II effector system may function in alternative contexts such as eukaryotic cells.

Using such systems, the inventors have shown effective Crispr-Cas9 targeting of Angiotensinogen (AGT) in vitro. In vivo, effective Crispr-Cas9 targeting of Angiotensinogen-II in liver hepatocytes was associated with significant reductions of blood pressure in rat models of hypertension. Further, the inventors observed reduced blood pressure in normotensive rats and that Crispr-Cas9 targeting of the liver Angiotensinogen (AGT) gene prevented low salt induced hypertension. Importantly, the effects on blood pressure were sustained and prolonged.

Accordingly, one aspect of the present disclosure provides a guide RNA (gRNA) that targets an angiotensinogen (AGT) gene and comprising, consisting of, or consisting essentially of a polynucleotide sequence corresponding to at least one of the sequences listed in Tables 1A, 1B, and/or 1C.

B. DNA Targeting Compositions

Another aspect of the present disclosure provides a DNA targeting composition comprising an endonuclease and at least one gRNA as provided herein. The DNA targeting compositions include at least one gRNA that targets an Angiotensiongen (ATG) gene (e.g., Angiotensinogen (ATG)-II gene), as described herein. The at least one gRNAs can bind and recognize a target region. The target regions can be chosen immediately upstream of possible out-of-frame stop codons such that insertions or deletions during the repair process restore the AGT reading frame by frame conversion. Target regions can also be splice acceptor sites or splice donor sites, such that insertions or deletions during the repair process disrupt splicing and restore the AGT reading frame by splice site disruption and exon exclusion. Target regions can also be aberrant stop codons such that insertions or deletions during the repair process restore the AGT reading frame by eliminating or disrupting the stop codon. Target regions may also be genes, or portions thereof, that are to be deleted or spliced out of the nucleic acid.

C. Compositions for Genome Editing and Deletion

Another aspect of the present disclosure provides a vector comprising, consisting of, or consisting essentially of at least one gRNA as provided herein and at least one endonuclease. In some embodiments, the vector comprises a viral vector. In one embodiment, the vector comprises an Adeno-associated virus (AAV) vector. The AAV vector is a small virus belonging to the genus Dependovirus of the Parvoviridae family that infects humans and some other primate species.

AAV vectors may be used to deliver CRISPR-based gene editing systems using various construct configurations. For example, AAV vectors may deliver endonucleases and gRNA expression cassettes as provided herein on separate vectors or on the same vector. In some embodiments, both the endonucleases and up to two gRNA expression cassettes as provided herein may be combined in a single AAV vector within the 4.7 kb packaging limit. In certain embodiments, the vector comprises an AAV-8 vector.

In another embodiment, the vector comprises at least one tissue-specific promoter operably linked to the polynucleotide sequence encoding at least one of the gRNA sequences or endonuclease as provided herein. In some embodiments, the tissue-specific promoter comprises a hepatocyte-specific promoter.

Another aspect of the present disclosure provides a modified adeno-associated viral vector for deleting and/or gene editing an Angiotensinogen (AGT) gene comprising, consisting of, or consisting essentially at least one polynucleotide sequence encoding a gRNA as provided herein and an endonuclease. In such cases, the modified AAV vector may have enhanced tropism for a particular cell (e.g., hepatocyte), tissue (e.g., liver tissue), organ (e.g., liver), etc.

Another aspect of the present provides a cell comprising, consisting of, or consisting essentially of at least at least one gRNA and/or a polynucleotide sequence encoding the same as provided herein, a composition as provided herein, or a vector as provided herein.

D. Pharmaceutical Compositions

The presently disclosed subject matter provides for compositions comprising the above-described genetic constructs. The pharmaceutical compositions according to the present invention can be formulated according to the mode of administration to be used. In cases where pharmaceutical compositions are injectable pharmaceutical compositions, they are sterile, pyrogen free and particulate free. An isotonic formulation is preferably used. Generally, additives for isotonicity may include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

The composition may further comprise a pharmaceutically acceptable excipient and/or carrier. The pharmaceutically acceptable excipient may be functional molecules as vehicles, adjuvants, carriers, or diluents. The pharmaceutically acceptable excipient may be a transfection facilitating agent, which may include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the composition for genome editing/deleting in in a cell (e.g., hepatocyte), tissue (e.g., liver tissue), or organ (e.g, liver), at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the DNA vector encoding the composition may also include a transfection facilitating agent such as lipids, liposomes, including lecithin liposomes or other liposomes known in the art, as a DNA-liposome mixture (see for example International Patent Publication No. WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid.

E. Methods of Delivery

Provided herein is are methods for delivering the presently disclosed genetic construct (e.g., a vector) or a composition thereof to a cell. The delivery of the compositions may be the transfection or electroporation of the composition as a nucleic acid molecule that is expressed in the cell and delivered to the surface of the cell. The nucleic acid molecules may be electroporated using BioRad Gene Pulser Xcell or Amaxa Nucleofector lib devices. Several different buffers may be used, including BioRad electroporation solution, Sigma phosphate-buffered saline product #D8537 (PBS), Invitrogen OptiMEM I (OM), or Amaxa Nucleofector solution V (N. V.). Transfections may include a transfection reagent, such as Lipofectamine 2000.

Upon delivery of the presently disclosed genetic construct or composition to the tissue, and thereupon the vector into the cells of the mammal, the transfected cells will express the gRNA(s) and the endonuclease. The genetic construct or composition may be administered to a mammal to alter gene expression or to re-engineer or alter the genome. For example, the genetic construct or composition may be administered to a mammal to correct, mutate, and/or delete the Angiotensinogen (AGT) gene in a mammal. The mammal may be human, non-human primate, cow, pig, sheep, goat, antelope, bison, water buffalo, bovids, deer, hedgehogs, elephants, llama, alpaca, mice, rats, or chicken, and preferably human, cow, pig, or chicken.

The genetic construct (e.g., a vector) encoding the gRNA(s) and the endonuclease can be delivered to the mammal by DNA injection (also referred to as DNA vaccination) with and without in vivo electroporation, liposome mediated, nanoparticle facilitated, and/or recombinant vectors. The recombinant vector can be delivered by any viral mode. The viral mode can be recombinant lentivirus, recombinant adenovirus, and/or recombinant adeno-associated virus.

A presently disclosed genetic construct (e.g., a vector) or a composition comprising thereof can be introduced into a cell to genetically delete an Angiotensinogen (ATG) gene (e.g., Angiotensinogen (ATG)-H gene). In certain embodiments, a presently disclosed genetic construct (e.g., a vector) or a composition comprising thereof is introduced into a hypatocyte cell from a patient suffering from hypertension, high bloods, or the like.

F. Routes of Administration

The presently disclosed genetic constructs (e.g., vectors) or a composition comprising thereof may be administered to a subject by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. In certain embodiments, the presently disclosed genetic construct (e.g., a vector) or a composition is administered to a subject (e.g., a subject suffering from hypertension, high blood pressure, etc.) intramuscularly, intravenously or a combination thereof. For veterinary use, the presently disclosed genetic constructs (e.g., vectors) or compositions may be administered as a suitably acceptable formulation in accordance with normal veterinary practice. The veterinarian may readily determine the dosing regimen and route of administration that is most appropriate for a particular animal. The compositions may be administered by traditional syringes, needleless injection devices, "microprojectile bombardment gone guns", or other physical methods such as electroporation ("EP"), "hydrodynamic method", or ultrasound.

The presently disclosed genetic construct (e.g., a vector) or a composition may be delivered to the mammal by several technologies including DNA injection (also referred to as DNA vaccination) with and without in vivo electroporation, liposome mediated, nanoparticle facilitated, recombinant vectors such as recombinant lentivirus, recombinant adenovirus, and recombinant adenovirus associated virus. The composition may be injected into the skeletal muscle or cardiac muscle. For example, the composition may be injected into the tibialis anterior muscle or tail.

In some embodiments, the presently disclosed genetic construct (e.g., a vector) or a composition thereof is administered by 1) tail vein injections (systemic) into adult mice; 2) intramuscular injections, for example, local injection into a muscle such as the TA or gastrocnemius in adult mice; 3) intraperitoneal injections into P2 mice; or 4) facial vein injection (systemic) into P2 mice.

G. Cell Types

Any of these delivery methods and/or routes of administration can be utilized with a variety of cell types. For example, the following cell types are preferentially targeted—hepatocytes, cells of the central nervous system (e.g., brain cells), cells of the heart and cardiovascular system (including cells of blood vessel walls), and kidney cells. For example, those cell types currently under investigation for cell-based therapies of hypertension, including, but not limited to, fibroblasts, induced pluripotent stem cells, bone marrow-derived progenitors, skeletal muscle progenitors, human skeletal myoblasts, CD 133+ cells, mesoangioblasts, cardiomyocytes, hepatocytes, chondrocytes, mesenchymal progenitor cells, hematopoetic stem cells, smooth muscle cells, or other progenitor cells. In some embodiments, the cells comprise hepatocytes.

H. Methods

The cells comprising at least one gRNA as provided herein, polynucleotide sequences encoding the DNA composition as provided herein, the vectors as provided herein, the compositions as provided herein, or the modified adeno-associated viral vectors provided herein may also be used in numerous methods for treating conditions associated with Angiotensinogen gene, such as hypertension, high blood pressure, etc.

Another aspect of the present disclosure provides a method of deleting an Angiotensinogen (AGT) gene comprising, consisting of, or consisting essentially of administering to a cell at least one gRNA as provided herein, a polynucleotide sequence encoding the DNA composition as provided herein, the vector as provided herein, the composition as provided herein, or the modified adeno-associated viral vector provided herein.

Another aspect of the present disclosure provides a method of treating a subject suffering from hypertension comprising, consisting of, or consisting essentially of administering to the subject at least one gRNA as provided herein, a polynucleotide sequence encoding the DNA composition as provided herein, the vector as provided herein, the composition as provided herein, or the modified adeno-associated viral vector provided herein.

Another aspect of the present disclosure provides a method of treating a subject suffering from high blood pressure in a subject comprising, consisting of, or consisting essentially of administering to the subject at least one gRNA as provided herein, a polynucleotide sequence encoding the DNA composition as provided herein, the vector as provided herein, the composition as provided herein, or the modified adeno-associated viral vector provided herein.

Diagnosis of High Blood Pressure (Hypertension)

Blood pressure (BP) is the pressure of circulating blood against the walls of blood vessels. Most of this pressure results from the heart pumping blood through the circulatory system. When used without qualification, blood pressure may refer to the pressure in the large arteries. Blood pressure is usually expressed in terms of the systolic pressure (maximum pressure during one heartbeat) over diastolic pressure (minimum pressure between two heartbeats) in the cardiac cycle. It is measured in millimeters of mercury (mm Hg) above the surrounding atmospheric pressure. High blood pressure, also called hypertension, is blood pressure that is higher than normal. The blood pressure of a person changes throughout the day based on the person's activities. Having blood pressure measures consistently above normal may result in a diagnosis of high blood pressure (or hypertension).

For diagnosis, systolic and/or diastolic blood pressure levels of a person may be measured. For some health care professionals, a person may have a normal blood pressure if the person's systolic blood pressure level is less than about 120 mm Hg and the person's diastolic blood pressure level is less than about 80 mm Hg. A person may have a risk of high blood pressure (prehypertension) when his or her systolic blood pressure level is about 120 mm Hg to 129 mm Hg (according to The 2017 American College of Cardiology/American Heart Association Guideline for the Prevention, Detection, Evaluation, and Management of High Blood Pressure in Adults), and his or her diastolic blood pressure level is less than about 80 mm Hg. A person may have a high blood pressure (hypertension) when his or her systolic blood pressure level is about 130 mm Hg or higher, and his or her diastolic blood pressure level is about 80 Hg or higher. In the category of hypertension, more levels may be divided, including high blood pressure (hypertension) stage 1 (usually having systolic blood pressure of about 130 to about 139 mm Hg and diastolic blood pressure of about 80 to about 89 mm Hg), high blood pressure (hypertension) stage 2 (usually having systolic blood pressure of about 140 mm Hg or higher and diastolic blood pressure of about 90 mm Hg or higher), and hypertensive crisis stage (usually having systolic blood pressure of about 180 mm Hg or higher and diastolic blood pressure of about 120 mm Hg or higher).

Most of the hypertension people are symptomless, while others may experience severe headache, shortness of breath, nosebleed, severe anxiety, feeling of pulsations in the neck or head, etc.

Traditionally, blood pressure was measured non-invasively using auscultation with either an aneroid gauge, or a mercury-tube sphygmomanometer. Auscultation is still generally considered to be the gold standard of accuracy for non-invasive blood pressure readings in clinic. However, semi-automated methods are also available, such as those using oscillometry.

Blood pressure is influenced by cardiac output, systemic vascular resistance and arterial stiffness and varies depending on situation, emotional state, activity, and relative health/disease states. In the short term, blood pressure is regulated by baroreceptors which act via the brain to influence the nervous and the endocrine systems. Hypertension may have many causes and may be of sudden onset or of long duration. Long-term hypertension is a risk factor for many diseases, including stroke, heart disease, and kidney failure.

The renin-angiotensin-aldosterone system (RAAS) is responsible for maintaining blood pressure and vascular tone. Modulation of the RAAS, therefore, interferes with essential cellular processes and leads to high blood pressure, oxidative stress, inflammation, fibrosis, and hypertrophy. Consequently, these conditions cause fatal cardiovascular and renal complications. Thus, the primary purpose of hypertension treatment is to diminish or inhibit overactivated RAAS. Currently available RAAS inhibitors, such as angiotensin-converting enzyme (ACE) inhibitors, angiotensin-receptor blockers (ARBs), and direct renin inhibitors, have proven effective in reducing blood pressure; however, evidence suggests that they may inadequately block the RAAS. In addition, RAAS inhibitors have some intolerable adverse effects, such as hyperkalemia and hypotension, which diminishes the value of these inhibitors especially for a prolonged use (e.g., for chronic hypertension patients). Some side effects of ACE-Inhibitors include a dry, non-productive cough, anemia, and functional renal insufficiency. Non-productive cough occurs in about 15% of people due to the accumulation of bradykinin in the system. Although rare, angioneurotic edema and hyperkalemia are potentially life-threatening adverse effects of ACE-Inhibitors. Hyperkalemia may develop as a result of potassium retention that is mediated by the reduction of aldosterone. The most common side effect of ARB's is renal insufficiency. ACE-Inhibitors and ARB's are not recommended for patients who are pregnant, or have a history of angioneurotic edema, hyperkalemia, or bilateral renal artery stenosis. By contrast, the instant disclosure provides an alternative therapy which can sufficiently block the RAAS without various side effects of current RAAS inhibitors, which is optimal for patients having chronic hypertension or suffering various side effects described herein.

Treatment for Elevated Blood Pressure

The present disclosure is based, in part, on the findings by the inventors of the effects of targeting the Crispr-Cas9 system to the machinery that directly regulates blood pressure; namely the Renin-Angiotensin-Aldosterone (RAAS) system. Accordingly, one aspect of the present disclosure provides a guide RNA (gRNA) that targets an angiotensinogen (AGT) gene and comprising, consisting of, or consisting essentially of a polynucleotide sequence corresponding to at least one of SEQ ID Nos: 1-3 or a complement thereof.

Various delivery systems may be used to edit genome using CRISPR-Cas9. The first and the most straightforward approach is to use a plasmid-based CRISPR-Cas9 system encoding the Cas9 protein and gRNA from the same vector, thus avoiding multiple transfections of different components (see Ran et al. 2013 Nature Protocols. 8:2281-2308). The second strategy is to deliver the mixture of the Cas9 mRNA and the gRNA (see Niu et al., 2014 Cell 156(4):836-843). The third strategy is to deliver the mixture of the Cas9 protein and the gRNA (see Zuris et al., 2015 Nat Biotechnol. 33(1):73-80). For a review on the delivery systems, see Liu et al. 2017 J Control Release 266: 17-26.

The plasmid-based CRISPR-Cas9 system is a simple and convenient strategy exhibiting greater stability than other systems. For instance, in the pX260 or pX330 system, Cas9 protein and gRNA are expressed form the same plasmid. The pX260 system, also known as the pX334 system, contains three cassettes, including a CRISPR RNA array, tracrRNA, and *S. pyogenes* Cas9 (or the Cas9 D10A nickase). The plasmid is digested with a restriction enzyme and then ligated with an annealed oligonucleotide that is designed for a specific targeting site. Another advanced system is called pX330 or pX335, which only contains two cassettes, a chimeric gRNA containing tracrRNA and *S. pyogenes* Cas9. Similarly, pX330 or pX335 vectors are also digested with restriction enzymes and used for ligation with annealed oligonucleotides that are designed for a specific targeting site. However, the plasmid-based system faces several challenges. First, the plasmid must be delivered into the nucleus. Secondly, the plasmid needs to be translated into Cas9 mRNA inside the cells, requiring more time for the target to be edited. On the other hand, delivery of the plasmid-based CRISPR-Cas9 systems produces more off-target effects. For example, delivery of a plasmid-based CRISPR-Cas9 system may generate small insertions and large insertions in off-target sites. The plasmid may be delivered by electroporation, hydrodynamic injection, microinjection, mechanical cell deformation, lipid nanoparticles, AAV, or lentivirus.

Direct delivery of the Cas9 mRNA and gRNA into target cells edits genome after expressing the Cas9 protein and subsequently forming the Cas9/gRNA complex inside the cells. The advantage of administering mRNAs is the transient expression of Cas9 protein, which limits the duration of gene-editing. In addition, delivery of mRNAs has lower off-target effects than the delivery of plasmid-based CRISPR-Cas9 system. Apart from subsiding off-target effects, mRNAs only need to enter the cytoplasm to exert their effects. Furthermore, the use of the mRNA encoding Cas9 protein shows low cytotoxicity in primary cells and cell lines. However, the relatively poor stability of mRNA is an obstacle for this type of gene-editing strategy. Delivery options include, e.g., electroporation, microinjection, and lipid nanoparticles.

Direct delivery of the Cas9 protein complexed with gRNA is the most widely studied strategy in recent years. The purified Cas9 protein is positively charged and can efficiently form a complex with sgRNA, which is called Cas9/sgRNA ribonucleoprotein complexes (RNPs). Direct delivery of RNPs has numerous advantages, including rapid action; high gene editing efficiency; no requirement of codon optimization and promoter selection; and reduced off-target effects, toxicity and immune responses. Delivery options include, e.g., electroporation, iTOP, lipid nanoparticles, polymer nanoparticles, CPP delivery, DNA nanostructure, and gold nanoparticles.

Methods of administration or delivery include any mode compatible with a subject. Methods and uses of the invention include delivery and administration systemically, regionally or locally, or by any route, for example, by injection or infusion. Such delivery and administration include parenterally, e.g. intraocularly, intravascularly, intravenously, intramuscularly, intraperitoneally, intradermally, subcutaneously, or transmucosal. Exemplary administration and delivery routes include intravenous (i.v.), intraperitoneal (i.p.), intrarterial, subcutaneous, intra-pleural, intubation, intrapulmonary, intracavity, iontophoretic, intraorgan, intralymphatic. In particular embodiments, an AAV vector is administered or delivered parenterally, such as intravenously, intraarterially, intraocularly, intramuscularly, subcutaneously, or via catheter or intubation.

Cas9 and one or more guide RNA can be delivered using adeno associated virus (AAV), lentivirus, adenovirus or other plasmid or viral vector types, in particular, using formulations and doses from, for example, U.S. Pat. No. 8,454,972 (formulations, doses for adenovirus), U.S. Pat. No. 8,404,658 (formulations, doses for AAV) and U.S. Pat. No. 5,846,946 (formulations, doses for DNA plasmids) and from clinical trials and publications regarding the clinical trials involving lentivirus, AAV and adenovirus. For examples, for AAV, the route of administration, formulation and dose can be as in U.S. Pat. No. 8,454,972 and as in clinical trials involving AAV. For Adenovirus, the route of administration, formulation and dose can be as in U.S. Pat. No. 8,404,658 and as in clinical trials involving adenovirus. For plasmid delivery, the route of administration, formulation and dose can be as in U.S. Pat. No. 5,846,946 and as in clinical studies involving plasmids. Doses may be based on or extrapolated to an average 70 kg individual, and can be adjusted for patients, subjects, mammals of different weight and species. Frequency of administration is within the ambit of the medical or veterinary practitioner (e.g., physician, veterinarian), depending on usual factors including the age, sex, general health, other conditions of the patient or subject and the particular condition or symptoms being addressed.

Several types of particle delivery systems and/or formulations are known to be useful in a diverse spectrum of biomedical applications. In general, a particle is defined as a small object that behaves as a whole unit with respect to its transport and properties. Particles are further classified according to diameter Coarse particles cover a range between 2,500 and 10,000 nanometers. Fine particles are sized between 100 and 2,500 nanometers. Ultrafine particles, or nanoparticles, are generally between 1 and 100 nanometers in size. The basis of the 100-nm limit is the fact that novel properties that differentiate particles from the bulk material typically develop at a critical length scale of under 100 nm.

The CRISPR enzyme, for instance a Cas9, and/or any of the present RNAs, for instance a guide RNA, can be delivered using adeno associated virus (AAV), lentivirus, adenovirus or other viral vector types, or combinations thereof. Cas9 and one or more guide RNAs can be packaged into one or more viral vectors. In some embodiments, the viral vector is delivered to the tissue of interest by, for example, an intramuscular injection, while other times the viral delivery is via intravenous, transdermal, intranasal, oral, mucosal, or other delivery methods. Such delivery may be either via a single dose, or multiple doses. One skilled in the art understands that the actual dosage to be delivered herein may vary greatly depending upon a variety of factors, such as the vector chose, the target cell, organism, or tissue, the general condition of the subject to be treated, the degree of transformation/modification sought, the administration route, the administration mode, the type of transformation/modification sought, etc.

Such a dosage may further contain, for example, a carrier (water, saline, ethanol, glycerol, lactose, sucrose, calcium phosphate, gelatin, dextran, agar, pectin, peanut oil, sesame oil, etc.), a diluent, a pharmaceutically-acceptable carrier (e.g., phosphate-buffered saline), a pharmaceutically-acceptable excipient, and/or other compounds known in the art.

Such a dosage formulation is readily ascertainable by one skilled in the art. The dosage may further contain one or more pharmaceutically acceptable salts such as, for example, a mineral acid salt such as a hydrochloride, a hydrobromide, a phosphate, a sulfate, etc.; and the salts of organic acids such as acetates, propionates, malonates, benzoates, etc. Additionally, auxiliary substances, such as wetting or emulsifying agents, pH buffering substances, gels or gelling materials, flavorings, colorants, microspheres, polymers, suspension agents, etc. may also be present herein. In addition, one or more other conventional pharmaceutical ingredients, such as preservatives, humectants, suspending agents, surfactants, antioxidants, anticaking agents, fillers, chelating agents, coating agents, chemical stabilizers, etc. may also be present, especially if the dosage form is a reconstitutable form. Suitable exemplary ingredients include microcrystalline cellulose, carboxymethylcellulose sodium, polysorbate 80, phenylethyl alcohol, chlorobutanol, potassium sorbate, sorbic acid, sulfur dioxide, propyl gallate, the parabens, ethyl vanillin, glycerin, phenol, parachlorophenol, gelatin, albumin and a combination thereof.

In an embodiment herein the delivery is via an adenovirus, which may be at a single booster dose containing at least $1 \times 10^5$ particles (also referred to as particle units, pu) of adenoviral vector. In an embodiment herein, the dose preferably is at least about $1 \times 10^6$, about $1 \times 10^7$, or about $1 \times 10^8$ particles of the adenoviral vector. Thus, the dose may contain a single dose of adenoviral vector with, for example, about $1 \times 10^6$ particle units (pu), about $2 \times 10^6$ pu, about $4 \times 10^6$ pu, about $1 \times 10^7$ pu, about $2 \times 10^7$ pu, about $4 \times 10^7$ pu, about $1 \times 10^8$ pu, about $2 \times 10^8$ pu, about $4 \times 10^8$ pu, about $1 \times 10^9$ pu, about $2 \times 10^9$ pu, about $4 \times 10^9$ pu, about $1 \times 10^{10}$ pu, about $2 \times 10^{10}$ pu, about $4 \times 10^{10}$ pu, about $1 \times 10^{11}$ pu, about $2 \times 10^{11}$ pu, about $4 \times 10^{11}$ pu, about $1 \times 10^{12}$ pu, about $2 \times 10^{12}$ pu, or about $4 \times 10^{12}$ pu of adenoviral vector. See, for example, the adenoviral vectors in U.S. Pat. No. 8,454,972 B2, incorporated by reference herein, and the dosages at col 29, lines 36-58 thereof. Dosages can range from $1 \times 10^5$ to $1 \times 10^{20}$ genome copies of AAV (also referred to as pu). Doses are determined by a physician and are customized based on circumstances of the individual to be treated. An exemplary treatment for hypertension or prehypertension of a human subject comprises administration of about $1$-$2 \times 10^{10}$ genome copies (or pu) of AAV per 60 kg individual. In some embodiments, a single treatment is used. In other embodiments, the adenovirus is delivered via multiple doses.

In an embodiment herein, the delivery is via an AAV. A therapeutically effective dosage for in vivo delivery of the AAV to a human is believed to be in the range of from about 20 to about 50 ml of saline solution containing from about $1 \times 10^5$ to about $1 \times 10^{10}$ functional AAV/ml solution. The dosage may be adjusted to balance the therapeutic benefit against any side effects. In an embodiment herein, the AAV dose is generally in the range of concentrations of from about $1 \times 10^5$ to $1 \times 10^{50}$ genomes AAV. A human dosage may be about $1 \times 10^{13}$ genomes AAV. Such concentrations may be delivered in from about 0.001 ml to about 100 ml, about 0.05 to about 50 ml, or about 10 to about 25 ml of a carrier solution. Other effective dosages can be readily established by one of ordinary skill in the art through routine trials establishing dose response curves. See, for example, U.S. Pat. No. 8,404,658 B2, at col. 27, lines 45-60.

In an embodiment herein the delivery is via a plasmid. In such plasmid compositions, the dosage should be a sufficient amount of plasmid to elicit a response. For instance, suitable quantities of plasmid DNA in plasmid compositions can be from about 0.1 to about 2 mg, or from about 1 µg to about 10 µg.

The doses herein are based on an average 70 kg individual. The frequency of administration is within the ambit of the medical or veterinary practitioner (e.g., physician, veterinarian), or scientist skilled in the art. Mice used in experiments are about 20 g. From that which is administered to a 20 g mouse, one can extrapolate to a 70 kg individual.

Several types of particle delivery systems and/or formulations are known to be useful in a diverse spectrum of biomedical applications. In general, a particle is defined as a small object that behaves as a whole unit with respect to its transport and properties. Particles are further classified according to diameter Coarse particles cover a range between 2,500 and 10,000 nanometers. Fine particles are sized between 100 and 2,500 nanometers. Ultrafine particles, or nanoparticles, are generally between 1 and 100 nanometers in size. The basis of the 100-nm limit is the fact that novel properties that differentiate particles from the bulk material typically develop at a critical length scale of under 100 nm.

As used herein, a particle delivery system/formulation is defined as any biological delivery system/formulation which includes a particle in accordance with the present invention. A particle in accordance with the present invention is any entity having a greatest dimension (e.g. diameter) of less than 100 microns (µm). In some embodiments, inventive particles have a greatest dimension of less than 10 µm. In some embodiments, inventive particles have a greatest dimension of less than 2000 nanometers (nm). In some embodiments, inventive particles have a greatest dimension of less than 1000 nanometers (nm). In some embodiments, inventive particles have a greatest dimension of less than 900 nm, 800 nm, 700 nm, 600 nm, 500 nm, 400 nm, 300 nm, 200 nm, or 100 nm. Typically, inventive particles have a greatest dimension (e.g., diameter) of 500 nm or less. In some embodiments, inventive particles have a greatest dimension (e.g., diameter) of 250 nm or less. In some embodiments, inventive particles have a greatest dimension (e.g., diameter) of 200 nm or less. In some embodiments, inventive particles have a greatest dimension (e.g., diameter) of 150 nm or less. In some embodiments, inventive particles have a greatest dimension (e.g., diameter) of 100 nm or less. Smaller particles, e.g., having a greatest dimension of 50 nm or less are used in some embodiments of the invention. In some embodiments, inventive particles have a greatest dimension ranging between 25 nm and 200 nm.

Particle characterization (including e.g., characterizing morphology, dimension, etc.) is done using a variety of different techniques. Common techniques are electron microscopy (TEM, SEM), atomic force microscopy (AFM), dynamic light scattering (DLS), X-ray photoelectron spectroscopy (XPS), powder X-ray diffraction (XRD), Fourier transform infrared spectroscopy (FTIR), matrix-assisted laser desorption/ionization time-of-flight mass spectrometry (MALDI-TOF), ultraviolet-visible spectroscopy, dual polarisation interferometry and nuclear magnetic resonance (NMR). Characterization (dimension measurements) may be made as to native particles (i.e., preloading) or after loading of the cargo (herein cargo refers to e.g., one or more components of CRISPR-Cas system e.g., CRISPR enzyme or mRNA or guide RNA, or any combination thereof, and may include additional components, carriers and/or excipients) to provide particles of an optimal size for delivery for any in vitro, ex vivo and/or in vivo application of the present invention. In certain preferred embodiments, particle dimension (e.g., diameter) characterization is based on measurements using dynamic laser scattering (DLS).

Particles delivery systems within the scope of the present invention may be provided in any form, including but not limited to solid, semi-solid, emulsion, or colloidal particles. As such any of the delivery systems described herein, including but not limited to, e.g., lipid-based systems, liposomes, micelles, microvesicles, exosomes, or gene gun may be provided as particle delivery systems within the scope of the present invention.

As used herein the term "pharmaceutically acceptable" and "physiologically acceptable" mean a biologically acceptable formulation, gaseous, liquid or solid, or mixture thereof, which is suitable for one or more routes of administration, in vivo delivery or contact. A "pharmaceutically acceptable" or "physiologically acceptable" composition is a material that is not biologically or otherwise undesirable, e.g., the material may be administered to a subject without causing substantial undesirable biological effects. Thus, such a pharmaceutical composition may be used, for example in administering a viral vector or viral particle to a subject.

Such compositions include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Pharmaceutical compositions can be formulated to be compatible with a particular route of administration or delivery, as set forth herein or known to one of skill in the art. Thus, pharmaceutical compositions include carriers, diluents, or excipients suitable for administration by various routes.

Compositions suitable for parenteral administration comprise aqueous and non-aqueous solutions, suspensions or emulsions of the active compound, which preparations are typically sterile and can be isotonic with the blood of the intended recipient. Non-limiting illustrative examples include water, saline, dextrose, fructose, ethanol, animal, vegetable or synthetic oils.

Co-solvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

A "unit dosage form" as used herein refers to physically discrete units suited as unitary dosages for the subject to be treated; each unit containing a predetermined quantity optionally in association with a pharmaceutical carrier (excipient, diluent, vehicle or filling agent) which, when administered in one or more doses, is calculated to produce a desired effect (e.g., prophylactic or therapeutic effect). Unit dosage forms may be within, for example, ampules and vials, which may include a liquid composition, or a composition in a freeze-dried or lyophilized state; a sterile liquid carrier, for example, can be added prior to administration or delivery in vivo. Individual unit dosage forms can be included in multi-dose kits or containers. Exemplary viral vectors, such as AAV vectors, and pharmaceutical compositions thereof can be packaged in single or multiple unit dosage form for ease of administration and uniformity of dosage.

I. Kits

Another aspect of the present disclosure provides a kit comprising, consisting of, or consisting essentially of cell comprising the cell comprising at least one gRNA and/or a polynucleotide sequence encoding the same as provided herein, a composition as provided herein, or a vector as provided herein, and instructions for use.

Instructions included in kits may be affixed to packaging material or may be included as a package insert. While the instructions are typically written or printed materials they are not limited to such. Any medium capable of storing such instructions and communicating them to an end user is contemplated by this disclosure. Such media include, but are not limited to, electronic storage media {e.g., magnetic discs, tapes, cartridges, chips), optical media {e.g., CD ROM), and the like. As used herein, the term "instructions" may include the address of an internet site that provides the instructions.

The kit can also optionally include one or more components, such as reagents required to use the disclosed compositions or to facilitate quality control evaluations, such as standards, buffers, diluents, salts, enzymes, enzyme co-factors, substrates, detection reagents, and the like. Other components, such as buffers and solutions for the isolation and/or treatment of the cells, also can be included in the kit. The kit can additionally include one or more other controls. One or more of the components of the kit can be lyophilized, in which case the kit can further comprise reagents suitable for the reconstitution of the lyophilized components.

In one aspect, the invention provides kits containing any one or more of the elements disclosed in the above methods and compositions. Elements may be provided individually or in combinations, and may be provided in any suitable container, such as a vial, a bottle, or a tube. In some embodiments, the kit includes instructions in one or more languages, for example in more than one language. Exemplary elements for packaging into the kit may include, at least, RNA and/or the protein components of the CRISPR-Cas9 system of the present invention, such as Cas9 mRNA, gRNA, and Cas9 protein, plasmids or other viral or non-viral vectors described herein to delivery the CRISPR-Cas9 system, and cells containing the CRISPR-Cas9 system, such as cells in which the angiotensinogen (AGT) gene is knockout by the CRISPR-Cas9 system of the present invention.

A kit may comprise one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. In some embodiments, the kit comprises one or more oligonucle-otides corresponding to a guide sequence for insertion into a vector so as to operably link the guide sequence and a regulatory element. In some embodiments, the kit comprises a homologous recombination template polynucleotide. In some embodiments, the kit comprises one or more of the vectors and/or one or more of the polynucleotides described herein. The kit may advantageously allow to provide all elements of the systems of the invention.

Another aspect of the present disclosure provides all that is described and illustrated herein.

The following Examples are provided by way of illustration and not by way of limitation.

1. Crispr-Cas9-Mediated Deletion of the Angiotensinogen Gene Reduces Hypertension

A. Methods

Materials and methods are described in the examples below. Reagents including AAV vectors (e.g., from Add-gene, Watertown, MA) and endonucleases, e.g., plasmids expressing CRISPR Cas9 nuclease (e.g., Addgene) are suitable for human administration and are publically-available from numerous sources/vendors.

B. AGT Gene Editing for Reduction of Blood Pressure

Studied were carried out to determine if targeting RAAS with Crispr-Cas9 would reduce blood pressure. To that end we targeted the first component of RAAS, Angiotensinogen (AGT). Four guide-RNAs (gRNAs) were designed to the first coding exon, exon 2, of the Angiotensinogen gene (FIGS. 1A-F).

Figure 1B:
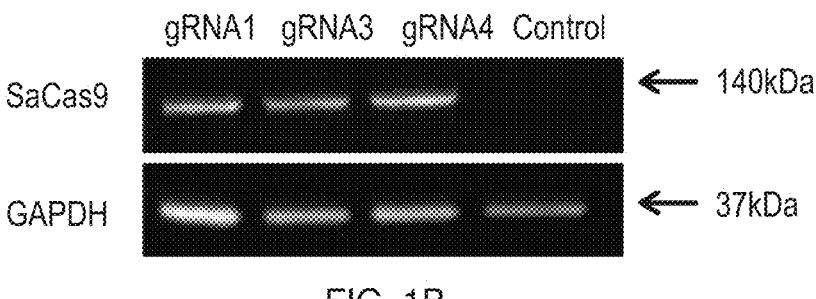
FIG. 1B is a photograph of an electrophoretic gel showing expression of Cas9-gRNA constructs in cultured hepatocytes. Four gRNAs that targeted Cas9 to the AGT gene were cloned into an AAV8 expression plasmid. Following infection of hepatocytes with the AAV8-Cas9-AGTgRNA constructs; protein extracts were analyzed for expression of the Cas9 protein. GADPH was used as a loading control. Representative images are shown. N=3.
Figure 1C:
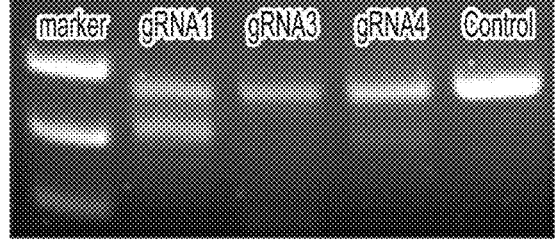
FIG. 1C is a photograph of an electrophoretic gel showing the results of analysis of Cas9 activity. One week after AAV8-Cas9-AGTgRNA infection, hepatocyte genomic DNA was isolated and analyzed for INDELs (insertions/deletions) via T7 endonuclease. Genomic DNA was amplified using specific primers flanking the cut site in the AGT gene. A representative image is shown. N=3.
Figure 1D:
FIG. 1D is a photograph of an electrophoretic gel showing that targeting the AGT gene reduces AGT protein expression in vitro. One week after AAV8-Cas9-AGTgRNA infection, hepatocyte protein extracts were analyzed for AGT expression. GADPH was used as a loading control. Representative images are shown. N=3.

The four gRNAs were then sub-cloned into a plasmid vector containing the expression cassette for Cas9. Of these four gRNAs, one (gRNA2), persistently failed to generate bacterial colonies and was discarded. The remaining three gRNA-Cas9 constructs were transiently transfected into cultured hepatocytes. Cas9 expression was robust (FIG. 1B). All three gRNAs led to efficient cleavage of the AGT gene; however, gRNA-1 and gRNA-4 displayed the greatest potency (FIG. 1C). As expected, all three gRNAs led to efficient knockdown of the AGT (FIG. 1D). Again, gRNA-4 had the greatest effect. As such, gRNA-4 was used for all subsequent experiments.

Figure 1E:
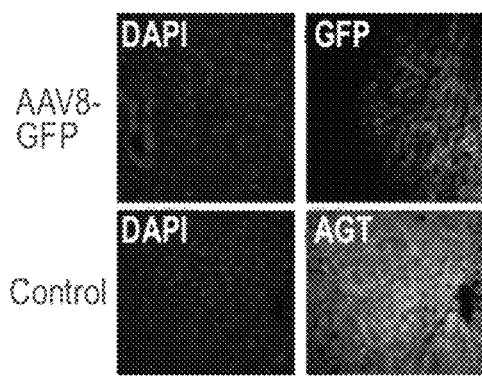
FIG. 1E is a photograph of an electrophoretic gel showing that AAV8 targets hepatocytes. AAV8-GFP was injected into the tail vein of SHR rats (characterized by spontaneous high blood pressure, adolescent onset). One week after injection, liver tissue was perfused, removed and sectioned. Liver sections were then analyzed for GFP and AGT expression. DAPI was used to visualize nuclei. Representative images are shown. N=3.
Figure 1F:
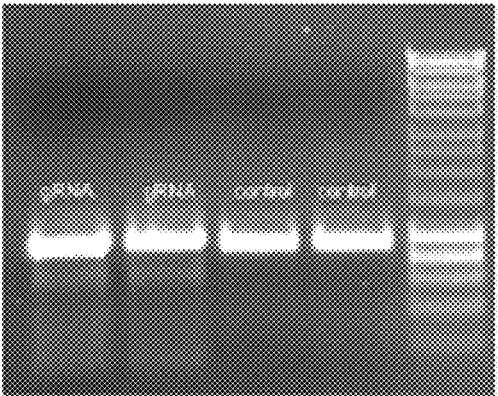
FIG. 1F is a photograph of an electrophoretic gel showing that AAV8-Cas9-AGTgRNA effectively cleaves the AGT gene in vivo. One week after tail-vein injection of the AAV8-Cas9-AGTgRNA into SHR rats, genomic DNA was isolated from the liver and analyzed for INDELs in the AGT gene. A representative image is shown. N=3.
Figure 2A:
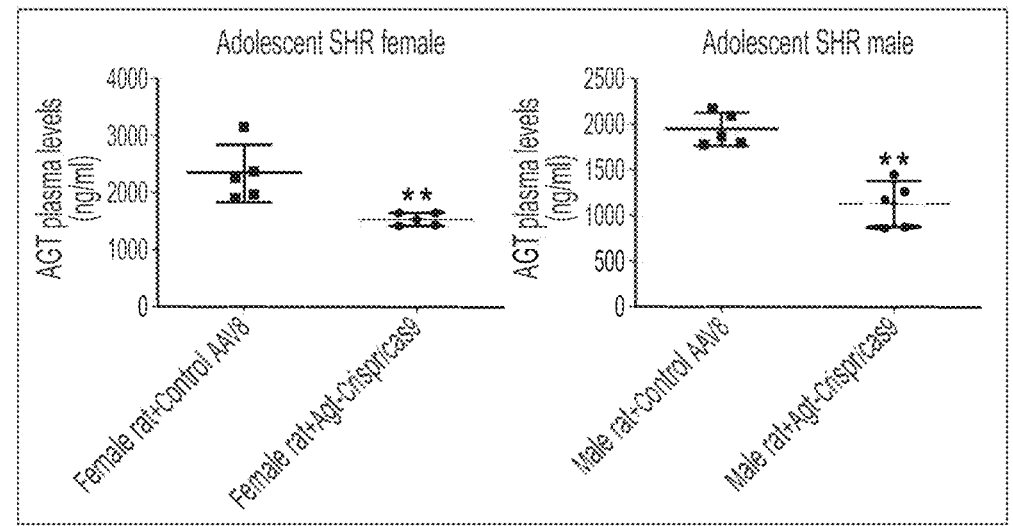
FIG. 2A, FIG. 2B, and FIG. 2C are graphs showing that AAV8-Cas9-AGTgRNA reduces circulating AGT levels. AAV8-Cas9-AGTgRNA was injected into the tail vein of (FIG. 2A) Adolescent SHR.
Figure 2B:
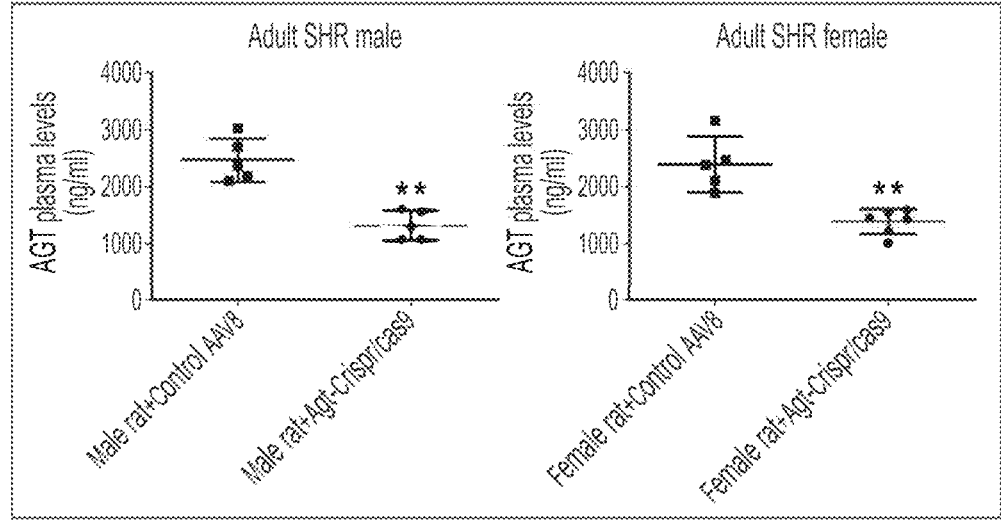
Figure 2C:
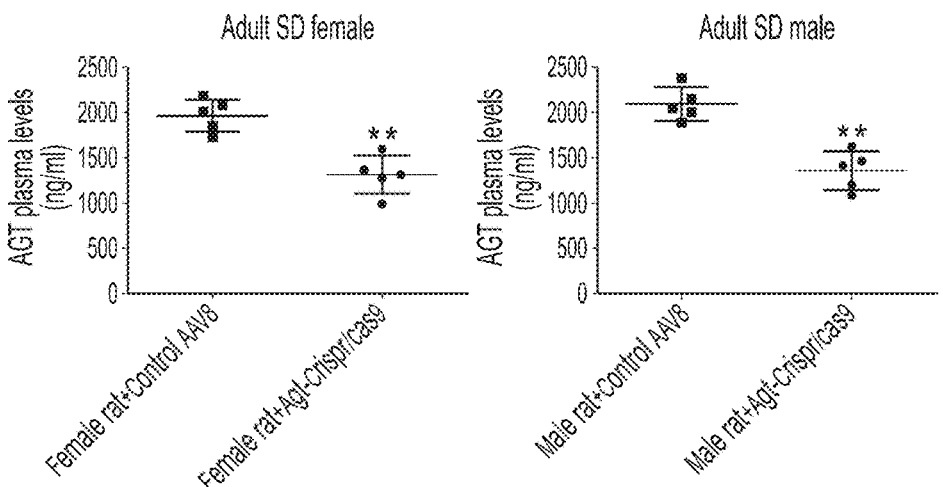

Hepatocytes are the major source of AGT in the body. Various AAV serotypes have been demonstrated to show cell selectivity. Consequently, we employed one serotype, AAV8, which has been shown to preferentially target hepa-tocytes. To carry out in vivo experiments, the Cas9-gRNA cassette was sub-cloned into an AAV plasmid and AAV8-Cas9-AGTgRNA particles subsequently generated. Injection of these AAV8-Cas9-AGTgRNA particles into the tail vein was effective in targeting the Cas9-AGTgRNA to the liver (FIG. 1E). Moreover, we observed robust cleavage of the AGT gene in the liver (FIG. 1F). Following the validation of the effectiveness of the AAV8-Cas9-AGTgRNA in targeting the AGT gene; circulating AGT levels were measured. We found that following injection of the AAV8-Cas9-AGTgRNA particles; AGT levels were significantly reduced in both SHR rats (FIGS. 2A and 2B) and SD rats (FIG. 2C). There was no significant difference with respect to sex, age or strain (FIGS. 2A-C).

Figure 3A:
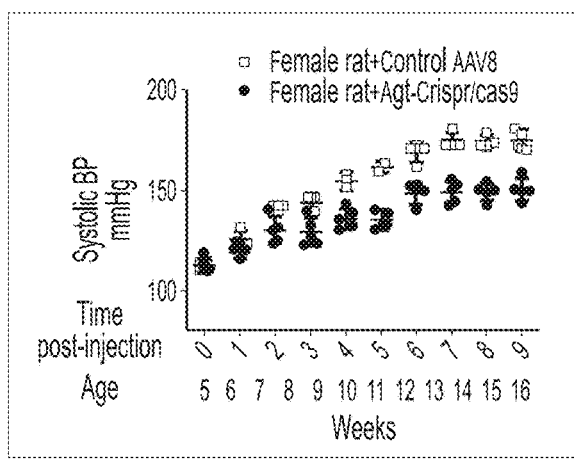
FIG. 3A is a graph showing the effect of treatment on blood pressure in a rat model. AAV8-Cas9-AGTgRNA was injected into the tail vein of adolescent (5-week old) female (top panels) and male (bottom panels) SHR rats. Blood pressure measurements were made by tail-cuff for up to 9 weeks post-injection. N=5 per group.
Figure 3A:
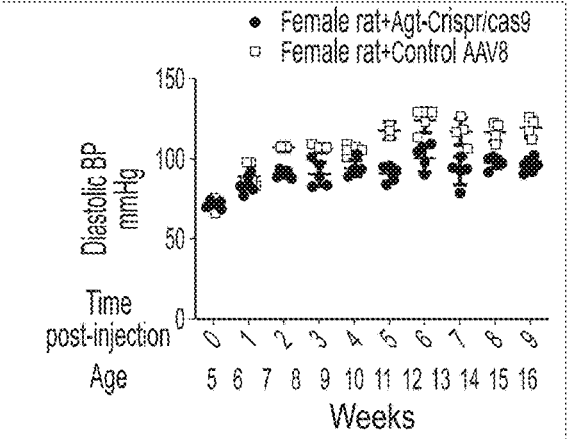
Figure 3A:
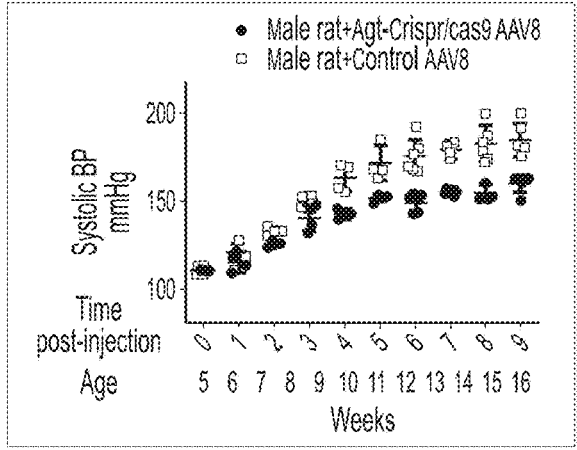
Figure 3A:
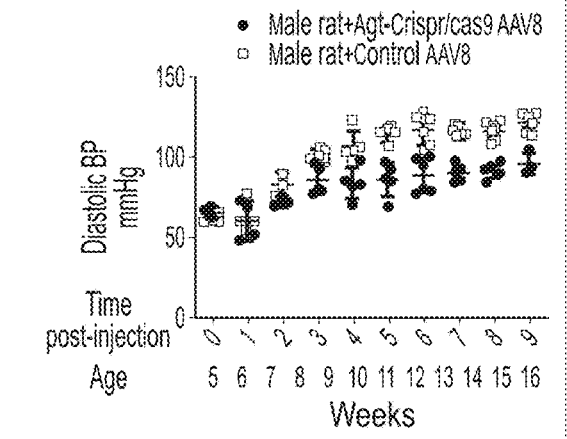

To measure the effects of AGT gene targeting upon blood pressure, the spontaneously hypertensive rat (SHR) model was first used. SHR rats begin to develop hypertension during adolescence. In control SHR rats, hypertension begins to be apparent around week 5 and progressively worsens over time (FIG. 3A). Notably, injection of AAV8-Cas9-AGTgRNA particles into 5 week old SHR rats significantly attenuated the progression of hypertension in these animals (FIG. 3A). This effect was observed in both female and male SHR rats; moreover, the effect was stronger on systolic versus diastolic blood pressure (FIG. 3A).

Figure 3B:
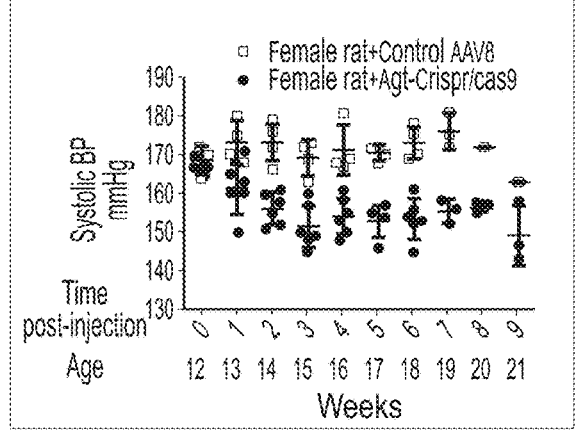
FIG. 3B is a graph showing the effect of treatment on blood pressure in a rat model. AAV8-Cas9-AGTgRNA was injected into the tail vein of adult (12-week old) female (top panels) and male (bottom panels) SHR rats. Blood pressure measurements were made by tail-cuff for up to 9 weeks post-injection. N=4-5 per group.
Figure 3B:
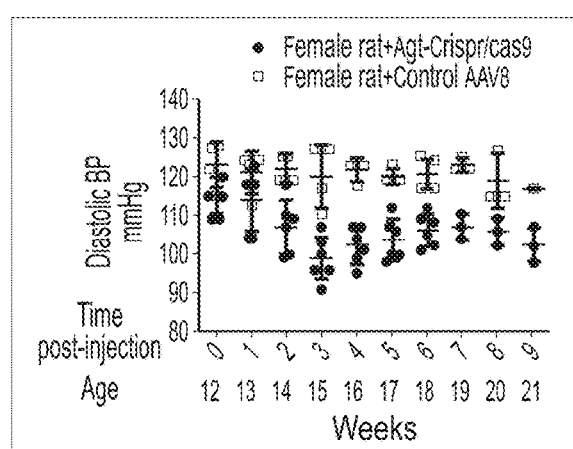
Figure 3B:
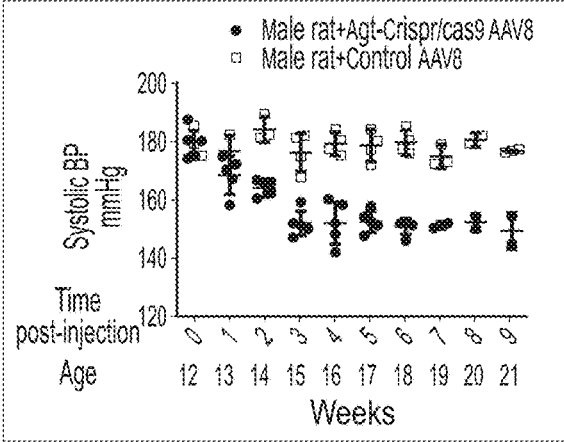
Figure 3B:
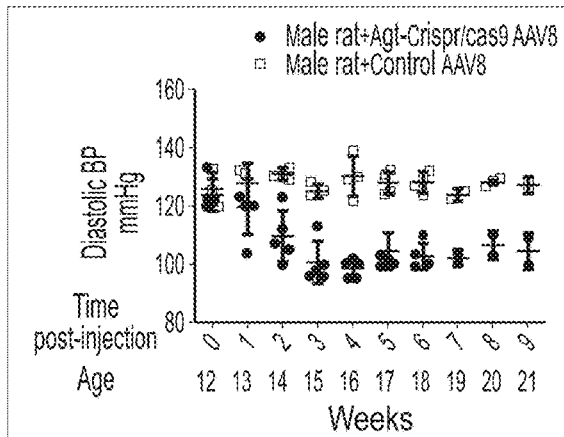
Figure 4A:
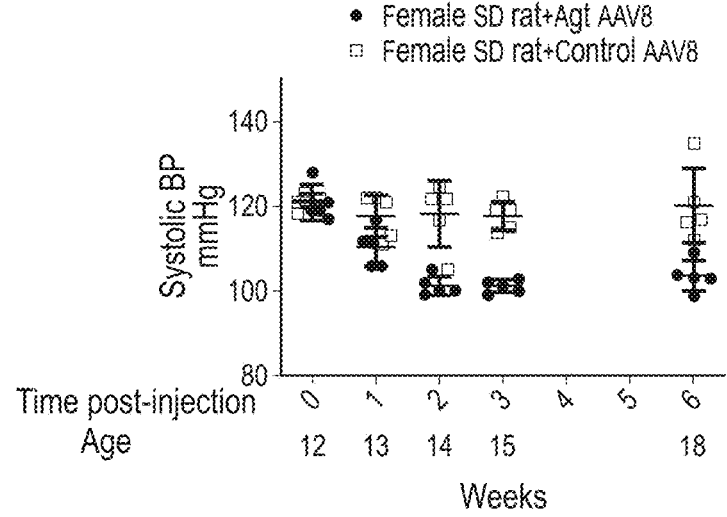
FIG. 4A, FIG. 4B, FIG. 4C, and FIG. 4D are graphs showing that AAV8-Cas9-AGTgRNA reduces blood pressure in normotensive and hypertensive 4D rats. AAV8-Cas9-AGTgRNA was injected into the tail vein of adult (12-week old) female (top panels) and male (bottom panels) SD rats. Blood pressure measurements were made by tail-cuff for up to 6 weeks post-injection. N=5 per group.
Figure 4B:
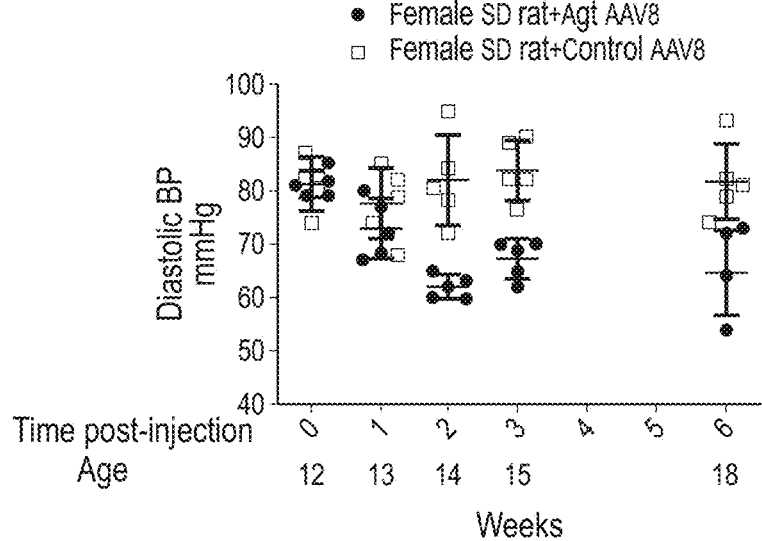
Figure 4C:
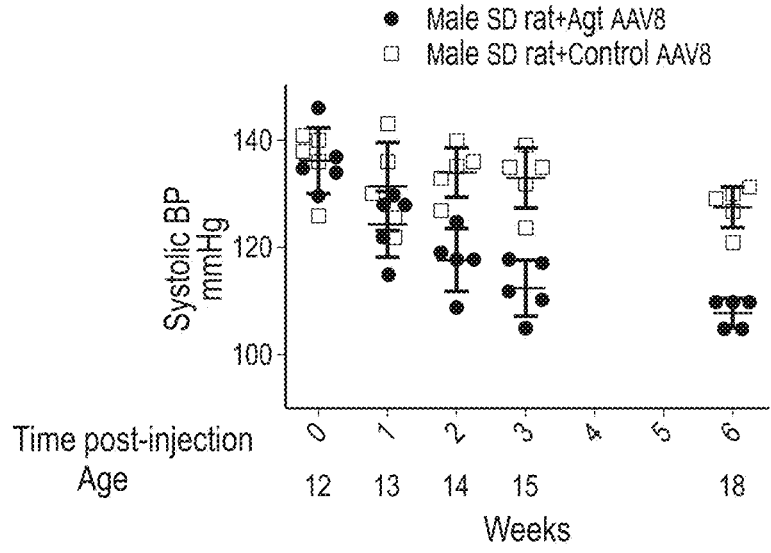
Figure 4D:
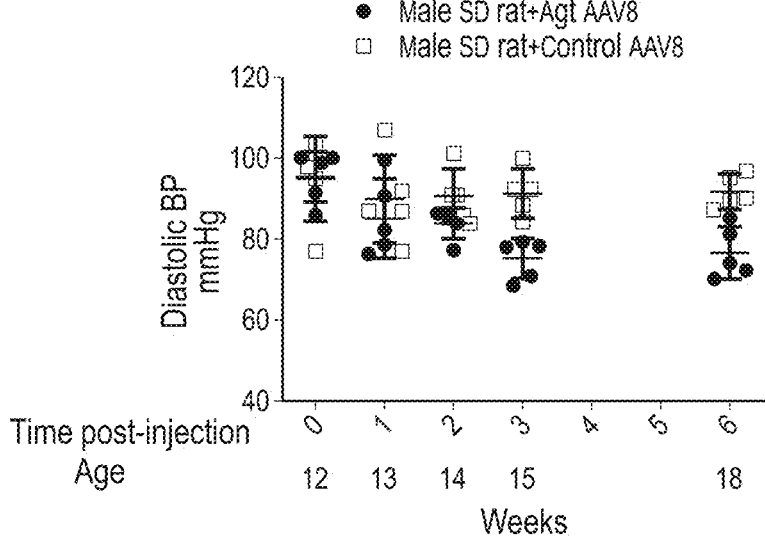

We then undertook studies to determine if AGT gene targeting would be effective in adult SHR rats with established hypertension. In control SHR rats, hypertension was apparent and sustained (FIG. 3B). In contrast, injection of AAV8-Cas9-AGTgRNA particles led to a rapid and progressive decrease in both systolic and diastolic blood pressure (FIG. 3B). Importantly, the reductions in blood pressure were sustained (FIG. 3B).

To ensure that our results were not strain dependent, we employed SD rats. Again, the injection of the AAV8-Cas9-AGTgRNA particles led to a rapid and sustained drop in both diastolic and systolic blood pressure in normotensive SD rats (FIGS. 4-D).

C. Crispr-Cas9 System to Target RAAS for Effective Control of Hypertension

To our knowledge, this is the first report of the Crispr-Cas9 system being employed to target RAAS for the effective control of hypertension. In general, the field has focused on siRNA approaches, which are associated with drawbacks. Considering the rapid degradation rate of siRNAs: typically, these siRNAs are expressed via AAVs. There are a number of benefits with an AAV expression system. Expression of the siRNA is maintained and AAVs do not incorporate into the genome. However, despite the advantages, there are several issues with AAV-siRNA based methods for the control of blood pressure. Firstly, AAVs can be removed from the organ via cell proliferation. This particularly important as the liver is a major organ for regulating blood pressure and liver cells are highly proliferative. Consequently, there is likely to be a need for repeated delivery of AAV-siRNA in human patients with hypertension. Second, persistent expression of siRNAs can induce the immune system. Chronic activation of the immune system can lead to the appearance of auto-immune diseases and in severe cases organ failure. In contrast, the Crispr-Cas9 system permanently affects the targeted gene (AGT). Moreover, as the effect is permanent, there is no need for continual expression of the Cas9 enzyme and no chronic effect on the immune system. Thus, Crispr-Cas9 mediated control of blood pressure is likely to be more applicable and beneficial in the clinic.

The studies and data described herein demonstrate that targeting RAAS with the Crispr-Cas9 system is an effective method to reduce blood pressure/treat hypertension as well as prehypertension.

2. gRNA Sequence Listing

The following gRNAs were designed and cloned into pX601 plasmid by using BsaI restriction enzyme. Their silence capacity was investigated in vitro in the rat C166 cell line. The following gRNA was employed to package the AAV virus to delete Agt in vivo:

Rat Primer: Forward:5'-CAC CGT GCT GTA GTA GAG
       GAGATG AA. (SEQ ID NO:9)
    Rat Primer: Reverse:5'-AAA CTT CAT CTC CTC TAC
       TAC AGCAC (SEQ ID NO:10)

The bold region comprises the overhang facilitating cloning. A single G nucleotide (underlined) was added to the 5' to enhance transcription from the U6 promoter 3. Crispr-Cas9-Mediated Deletion of the Angiotensinogen Gene Reduces Hypertension

A. Hypertension—Major Contributor to the Global Burden of Disease

Hypertension is a major contributor to the global burden of disease. Unfortunately, hypertension is controlled in less than one fifth of patients worldwide due to poor medication compliance resulting from the need to take one or more drugs, often several times daily and side-effects. An ideal therapeutic would be administered one time only and yield life-long blood pressure control. We investigated the hypothesis that Crispr-Cas9 mediated disruption of a key gene in the Renin-Angiotensin-Aldosterone-System RAAS, AGT, specifically in the liver, would result in sustained, and possibly life long, reduction in blood pressure. We demonstrated in vitro, that the Crispr-Cas9 system led to a significant reduction in AGT expression in hepatocytes. Delivery of the Crispr-Cas9 system into the liver via the hepatocyte-targeting AAV8 reduced both AGT expression (40% decrease) and circulating AGT levels (30% decrease). In the art-recognized SHR model of hypertension, Crispr-Cas9 mediated loss of AGT expression reduced blood pressure in adult animals with established hypertension and prevented the spontaneous development of hypertension in young SHR. Moreover, reductions in blood pressure were prolonged and sustained up to one year of follow up. In addition, the partial disruption of the hepatic AGT gene was sufficient to control hypertension but did not affect the homeostatic response to cardiovascular stress such as sodium depletion and furosemide. In summary, we have demonstrated that targeting the Crispr-Cas9 system to hepatic AGT results in sustained reduction of blood pressure. The compositions and methods described herein achieve sustained reductions in blood pressure and are useful for life-long and safe control of hypertension.

B. Methods

Animal models: Wistar Kyoto (WKY) and Spontaneously Hypertensive (SHR) rats were purchased from Charles River (Wilmington, MA, USA). WKY rats are the control for SHR rats. SHR were outbred from WKY (a WKY male with marked elevation of blood pressure was mated to female with slightly elevated blood pressure. Brother x sister mating with continued selection for spontaneous hypertension was then started until they had generated a colony of SHR0. A WKY rat with a number of spontaneous mutations that gave rise to high blood pressure was identified and used make the SHR.

All studies were approved by the Duke University Division of Laboratory Animals (DLAR) and the Duke Institutional Animal Care and Use Committee (IACUC). Protocol number is A056-19-03. Crispr-Cas9: sgRNA sequences were designed using online software provided by Benchling (Table 1). Plasmids: pX601-AAV-CMV: NLS-SaCas9-NLS-3xHA-bGHpA; U6: BsaI-sgRNA and pX6C1-GFP were obtained from Addgene. The paired gRNAs were synthesized and annealed according to standard protocols. Once annealed, the gRNAs were cloned into the vector by using BsaC restriction site.

In an exemplary method for the rat studies, the guide RNA was cloned into PX601 (Addgene #61591), and pAAV2/8 (Addgene #112864), pAdDeltaF6 (Addgene #112867), and pX601 (Addgene #61591) were employed to package AAV.

An exemplary preferred guide RNA to target AGT gene of the rat is TGCTGTAGTAGAGGAGATGAA (SEQ ID NO:11), and an exemplary preferred guide RNA to target AGT gene of the human is CCTTCCACCTCGTCATC-CACA (SEQ ID NO: 1). Primer pairs to make the gRNAs described herein are provided in the tables below.

TABLE 1A

| Primer sequences used in the study (Rat) | | |
|---|---|---|
| Primer name | Primer sequence (5'-3') (forward/reverse) | SEQ ID No. |
| gRNA1-forward | CAC CGT GCT GTA GTA GAG GAG ATG AA | 9 |
| gRNA1-reverse | AAA CTT CAT CTC CTC TAC TAC AGC AC | 10 |
| gRNA2-forward | CAC CGGT CTG GCT GCT GCT TCC ACC | 12 |
| gRNA2-reverse | AAA CGG TGG AAG CAG CAG CCA GACC | 13 |
| gRNA3-forward | CAC CGT AGT AGA GGA GAT GAA AGG G | 14 |
| gRNA3-reverse | AAA CCC CTT TCA TCT CCT CTA CTA C | 15 |
| T7-forward | AAG CAA GTC CAC AGA TCC GTG A | 16 |
| T7-reverse | CTC TGT CCC TCT CAC GCA TGA A | 17 |
| ITR primer-forward | GGAACCCCTAGTGATGGAGTT | 18 |
| ITR primer-reverse | CGGCCTCAGTGAGCGA | 19 |

TABLE 1B

| Primer sequences used for rat AGT | | |
|---|---|---|
| Primer name | Primer sequence (5'-3') (forward/reverse) | SEQ ID No. |
| gRNA1-forward | CAC CGT GCT GTA GTA GAG GAG ATG AA | 9 |
| gRNA1-reverse | AAA CTT CAT CTC CTC TAC TAC AGC AC | 10 |
| gRNA2-forward | CAC CGGT CTG GCT GCT GCT TCC ACC | 12 |
| gRNA2-reverse | AAA CGG TGG AAG CAG CAG CCA GACC | 13 |
| gRNA3-forward | CAC CGT AGT AGA GGA GAT GAA AGG G | 14 |
| gRNA3-reverse | AAA CCC CTT TCA TCT CCT CTA CTA C | 15 |

TABLE 1C

| Primer sequences used for human AGT | | |
|---|---|---|
| Primer name | Primer sequence (5'-3') (forward/reverse) | SEQ ID No. |
| gRNA1-forward | CAC CGC CTT CCA CCT CGT CAT CCA CA | 20 |
| gRNA1-reverse | AAA CTG TGG ATG ACG AGG TGG AAG GC | 21 |
| ERNA2-forward | CAC CGT CAT TGT GGA TGA CGA GGT GG | 22 |
| gRNA2-reverse | AAA CCC ACC TCG TCA TCC ACA ATG AC | 23 |
| gRNA3-forward | CAC CGA TAT TTC AGG GTA TGC GGA A | 24 |
| gRNA3-reverse | AAA CTT CCG CAT ACC CTG AAA TATC | 25 |

BRL 3A rat liver cell line culture: BRL 3A cell line was purchased from ATCC (ATCC® CRL-1442). The cells were cultured in DMEM (ThermoFisher) supplemented with 10% fetal bovine serum (ThermoFisher). Cells were used between passages 3 and 5. Transfection in vitro: BRL3A cells were transfected with pX601-GFP plasmids containing the gRNAs via Lipofectamine® 2000 Reagent (ThermoFisher). The transfection was carried out according to the manufacturer's instructions.

Genomic DNA isolation: Genomic DNA was purified by DNeasy Blood & Tissue Kits following the manufacturer's instructions (Genessee). DNA was amplified by Q5® Hot Start High-Fidelity 2× Master Mix (NEB) according to the manufacturer's instructions.

Indel assay; The ~1 kb amplicons of target sites were purified and digested by T7 Endonuclease I (NEB) following the manufacturer's recommendations. Digestions were then electrophoresed on a 2% w/v agarose gel and imaged on a gel imager (Bio-Rad).

Immunoblotting: Rat liver was isolated, cut into small pieces, and minced via a turrax homogenizer. Following homogenization, the minced tissue was lysed by adding ⅒th volume of 10× lysis buffer (625 mM Tris pH7.4; 10% v/v SDS; 10× Protease Inhibitor Cocktail-I (Sigma)). Samples were lysed by repeated passaging through a 25-gauge needle. The supernatant containing the cellular protein was then cleared of insoluble debris via centrifugation (14,000 g, 4° C., 10 min). The Bradford assay method was used to determine the protein concentration. Cellular protein (20-g per sample) was first electrophoresed on 4-12% SDS-PAGE gel (ThermoFisher) and then transferred to a PVDF membrane. The PVDF membrane was then incubated with a anti-AGT antibody (1:1000, Abcam) in antibody incubation buffer (5% w/v fat-free milk powder, 20 mM Tris-HCl pH7.4, 133 mM NaCl). An anti-GAPDH monoclonal antibody (1:2000; Cell signaling technology) was used as an internal loading control. Proteins were visualized via ECL-Prime (GE Healthcare).

Delivery of the gene-editing machinery in vivo: To generate AAV8 viral particles, 293T cells in a 15 cm dish (1 million cells, culture media: DMEM supplemented with 10% v/v fetal bovine serum) were transfected with AAV vectors, e.g., pAAV2/8 (Addgene #112864), pAdDeltaF6 (Addgene #112867), and pX601 (Addgene #61591). The AAV vectors described herein, e.g., those obtained from Addgene, are suitable for human administration.

Seventy-two hours later, media was removed and AAV particles were purified by Iodixanol gradient ultracentrifugation method (Millipore Sigma) according to the manufacturer's instructions. The viral particles were further concentrated by Amicon® Ultra-15 centrifugal filter units (Millipore Sigma) according to the manufacturer's instructions. Viral titers were determined via a PCR based method utilizing the primers listed in Table 1. The AAV8 viral particles ($2.0 \times 10^{12}$ genome copies/rat diluted in 400 µl PBS) were injected into a lateral tail vein.

AGT, ANGI, ANGII, renin activity assays: Whole blood was collected from rat tail vein into tubes with EDTA at pre-set time-point. It was centrifugated for 15 minutes at 2,000×g to get plasma. ANGI and ANGII ELISA kits were purchased from Enzo. AGT ELISA kit was from NOVUS biologicals. Rat renin activity fluorometric assay kit was from BioVision. All assays were performed according to the manufacturer's instructions.

Blood pressure measurements: The CODA™ Monitor rat tail-cuff system (Kent Scientific Corporation) was employed to measure the rat blood pressure in accordance with manufacturer's protocol. Firstly, rat was trained to get used to the measurement one week before AAV injection. They were restrained by clear holders with a dark nosecone and the values were obtained while non-sedated. Three readings were obtained and averaged.

Low salt diet and furosemide regimen: animals were provided with NaCl (0.02% w/v) and furosemide (2.28 mmol/L) in their drinking water for 10 days. The standard diet contained 0.4% NaCl.

Statistical Analysis: All experiments were performed at least 3 times. Each individual experiment was an average of a technical triplicate. Data were analyzed GraphPad Prism Version 5.0. Student's t-test and ANOVA were used to examine differences between groups. The results were expressed as mean±standard deviation (SD). Values were considered significantly different if $p<0.05$.

C. Targeting the RAAS with Crispr-Cas9 Reduces Blood Pressure

Figure 5A:
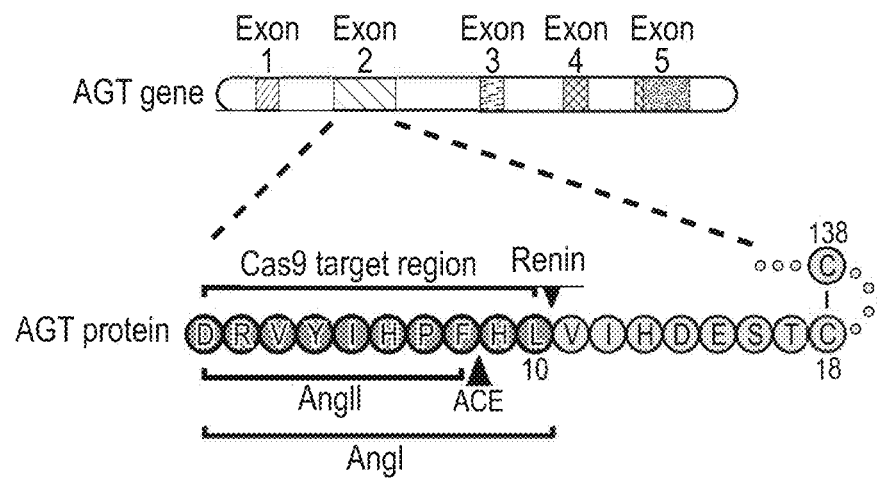
FIG. 5A is a schematic diagram of the AGT gene and the region targeted by the gRNAs used in this study. Coding exons (e.g., Exon 2) are shown in dark gray. Exons that give rise to untranslated regions are shown in light gray. A portion of the amino acid sequence encoded by Exon 2 is shown under the exon map, and the Cas target region (DRVYIHPFHL SEQ ID NO:4, shown in dark outlined circles) is and designated with a bracket. AGT is cleaved into AngI fragment by the enzyme, Renin, as indicated by a down arrow, and AGT is cleaved into AngII fragment by the enzyme, ACE, as indicated by an up arrow.

Studies were undertaken to determine whether targeting the RAAS with Crispr-Cas9 would reduce blood pressure. To that end, the first component of RAAS, Angiotensinogen (AGT) in the liver was targeted. Three guide-RNAs (gRNAs) were designed to the first coding exon, exon 2, of the Angiotensinogen gene (FIG. 5A).

Figure 5B:
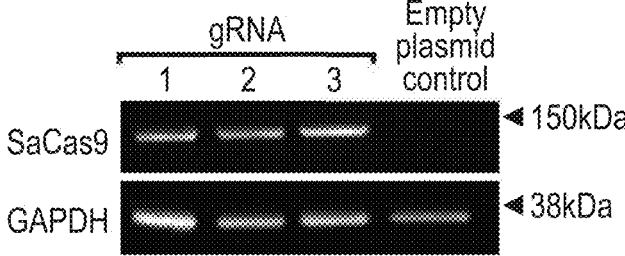
FIG. 5B is a photograph of an electrophoretic gel showing the expression of Cas9-gRNA constructs in cultured hepatocytes. gRNAs targeting Cas9 to the AGT gene were cloned into an AAV8 expression plasmid. An empty vector was used as a control. Following infection of hepatocytes with the AAV8-Cas9-AGTgRNA constructs; protein extracts (20 µg) were analyzed for expression of the Cas9 protein. GADPH was used as a loading control. Representative images are shown. N=3.
Figure 5C:
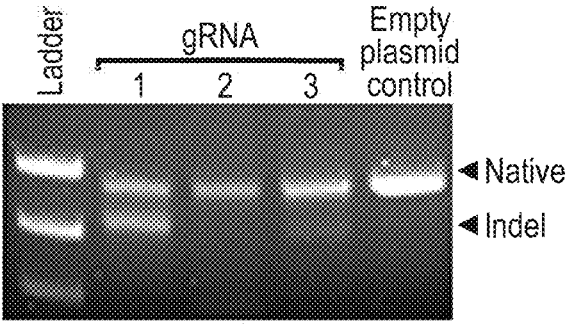
FIG. 5C is a photograph of an electrophoretic gel showing the results of an analysis of Cas9 activity in vitro. One week after AAV8-Cas9-AGTgRNA infection, hepatocyte genomic DNA was isolated and analyzed for INDELs (insertions/deletions) via T7 endonuclease. Genomic DNA was amplified using specific primers flanking the cut site in the AGT gene. A representative image is shown. N=3.

The gRNAs were then sub-cloned into a plasmid vector containing the expression cassette for Cas9. Once sub-cloned, the gRNA-Cas9 constructs were transiently transfected into cultured hepatocytes. Cas9 expression was robust (FIG. 5B). All three gRNAs led to efficient cleavage of the AGT gene; however, gRNA-1 displayed the greatest potency (FIG. 5C). All future experiments used gRNA-1.

Figure 5D:
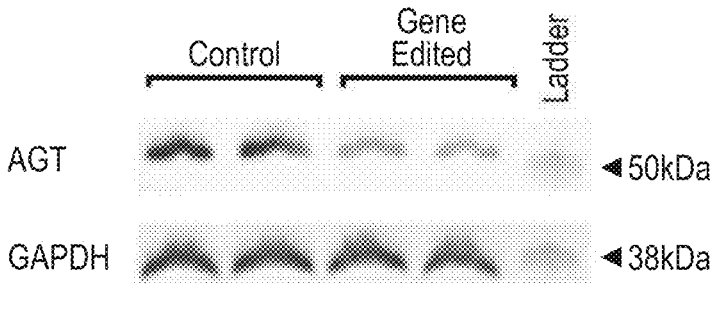
FIG. 5D is a photograph of an immunoblot showing level of AGT gene expression. AAV8-Cas9-AGTgRNA ($2\times10^{12}$ viral particles) was injected into the tail vein of 12-week old SHR. Control animals received an equivalent dose of AAV8-Cas9. One week after infection, liver tissue was analyzed for the expression of AGT protein (20 mg) by immunoblotting. GAPDH was used as a loading control. N=3. Representative image shown.
Figure 5E:
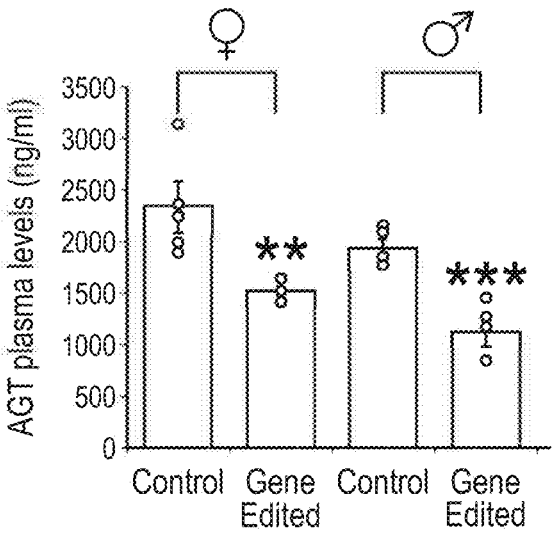
FIG. 5E and FIG. 5F are graphs showing ACT plasma levels. AAV8-Cas9-AGTgRNA ($2\times10^{12}$ viral particles) was injected into the tail vein of (E) 5-week old adolescent SHR and (F) 12-week old adult SHR. Control animals received an equivalent dose of AAV8-Cas9. One week after injection, blood was removed by tail-vein and plasma analyzed for AGT levels by ELISA. N=5 per group. P<0.01, *P<0.001.
Figure 5F:
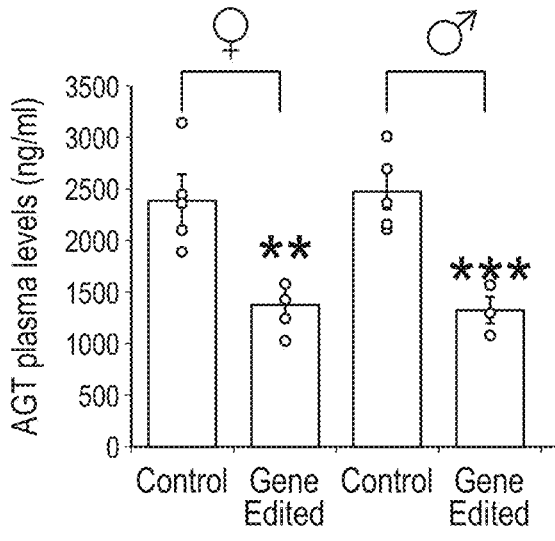
Figure 5G:
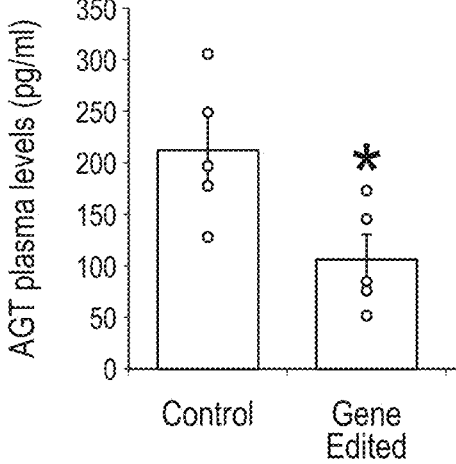
FIG. 5G is a graph showing AngI plasma levels.
Figure 5H:
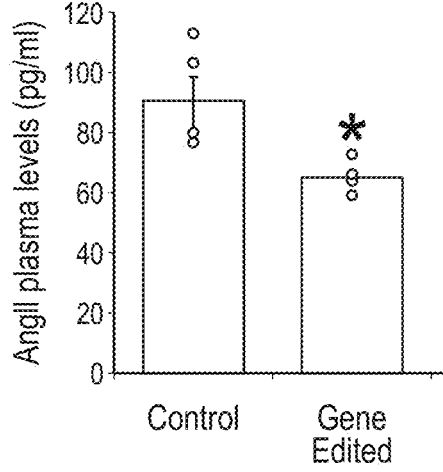
FIG. 5H is a graph showing AngII plasma levels.
Figure 5I:
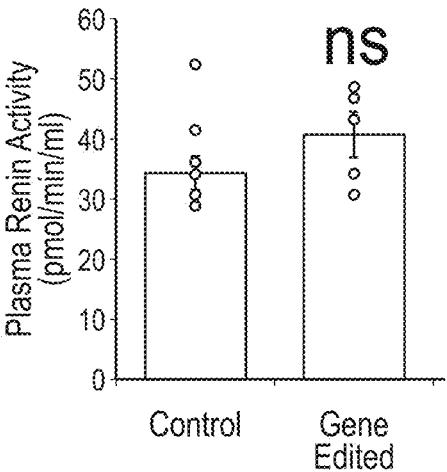
FIG. 5I is a graph showing plasma Renin activity levels. In each of FIG. 5G, FIG. 5H, and FIG. 5I, AAV8-Cas9-AGTgRNA ($2\times10^{12}$ viral particles) was injected into the tail vein of 12-week old adult SHR. Control animals received an equivalent dose of AAV8-Cas9. One week after injection, blood was removed by tail-vein and plasma analyzed for Angiotensinogen-I (AngI) levels, Angiotensinogen-II (AngII) levels and Renin activity by ELISA. N=5 per group. *P<0.05, P<0.01, *P<0.001.
Figure 10:
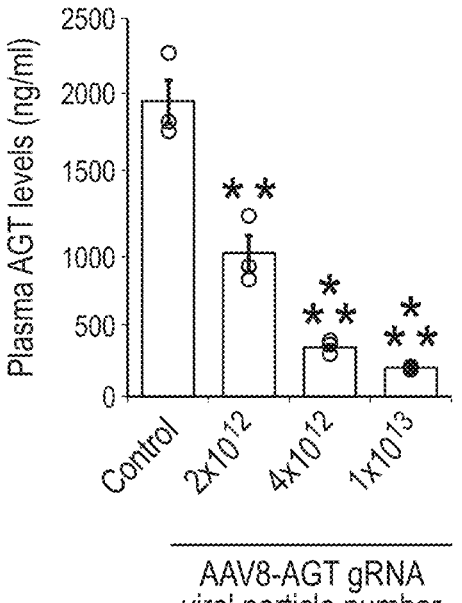
FIG. 10 is a bar graph showing optimization of the AAV8 dose. The indicated doses of AAV8-Cas9-AGTgRNA were injected into the tail vein of adult male SHR. AGT levels were measured by ELISA 4-weeks after injection. N=3 per group. P<0.01, *P<0.001.

Since hepatocytes are the major source of circulating AGT in the body, we targeted the liver for ablation of Angiotensinogen. Various AAV serotypes have been demonstrated to show cell selectivity. Consequently, we employed one serotype, AAV8, which has been shown to preferentially target hepatocytes. To carry out in vivo experiments, the Cas9-gRNA cassette was sub-cloned into an AAV plasmid and AAV8-Cas9-AGTgRNA particles subsequently generated. To measure the effects of AGT gene targeting on blood pressure, the spontaneously hypertensive rat (SHR) model was used. SHR develop hypertension during adolescence. Experiments with a GFP tracer indicated that AAV8 localized expression to the liver hepatocytes. Moreover, the viral dose was optimized to give rise to ~50% depletion of circulating AGT levels (FIG. 10) as complete disruption of the AGT gene would likely render the SHR hypotensive. Injection of these AAV8-Cas9-AGTgRNA particles into the tail vein was effective in reducing AGT protein levels in the liver (FIG. 5D). Following Cas9 cleavage of the genomic DNA the nuclear machinery repairs the damage by removing a random number of nucleotides. When the repair removes three nucleotides (one codon), or multiples thereof, the reading frame will stay in-frame and a protein produced. To validate the immunoblotting results, circulating AGT levels were measured. We found that 2 weeks following injection of the AAV8-Cas9-AGTgRNA particles; liver AGT levels were significantly reduced in both adolescent SHR (FIG. 5E) and adult SHR (FIG. 5F). Concomitant with a loss in AGT expression, plasma levels of both AngI and AngI were reduced in the gene edited SHR (FIG. 5G and FIG. 5H). There no effect on plasma renin activity (FIG. 5I).

Figure 6A:
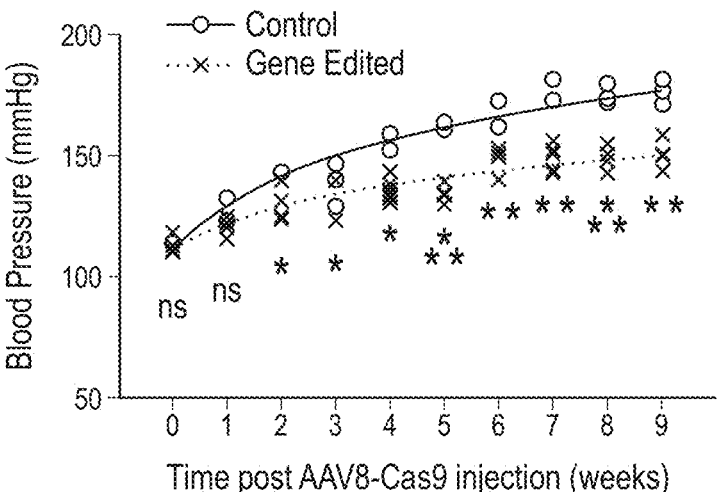
FIGS. 6A-D are line graphs showing that AGT gene editing prevents the acquisition of high blood pressure in the spontaneously hypertensive rat. AAV8-Cas9 (control) or AAV8-Cas9-AGTgRNA (gene-editing) viral particles ($2\times10^{12}$ viral particles) were injected into the tail vein of adolescent (5-week old) female (FIGS. 6A-B) and male (FIGS. 6C-D) SHR. Blood pressure measurements were made by tail-cuff for up to 9 weeks post-injection. N=4-5 per group. *P<0.05, P<0.01, *P<0.001. The mean of the control and gene-edited groups is shown by the solid and dashed line respectively.
Figure 6B:
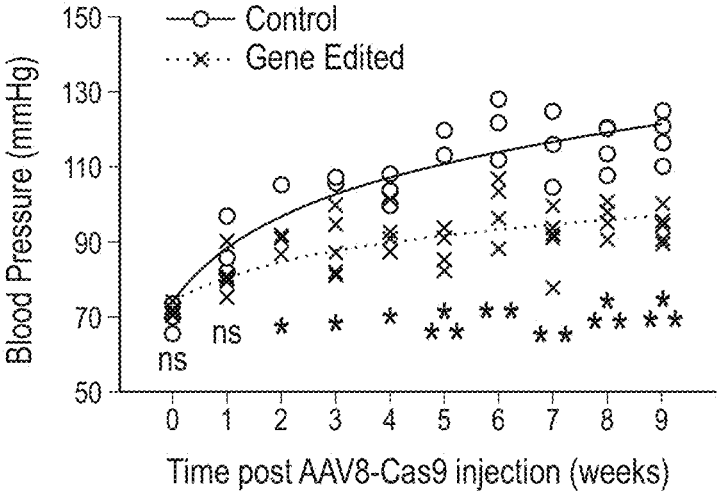
Figure 6C:
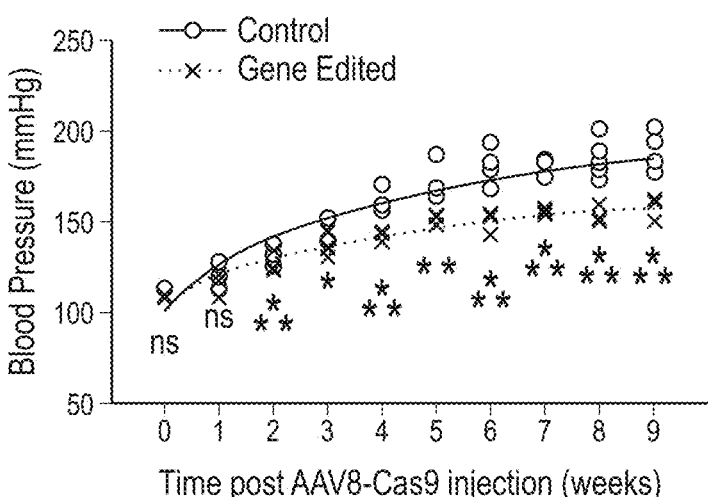
Figure 6D:
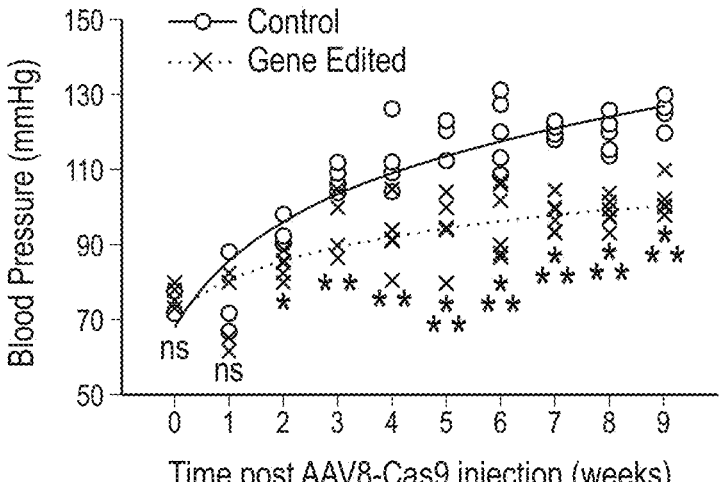
Figure 6E:
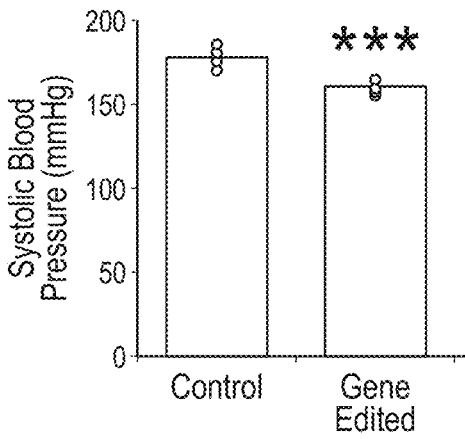
FIG. 6E is a bar graph showing the results of analysis of blood pressure 1 year after AAV8-Cas9 (control) or AAV8-Cas9-AGTgRNA (gene-editing) viral particle injection. N=4. ***P<0.001.
Figure 7A:
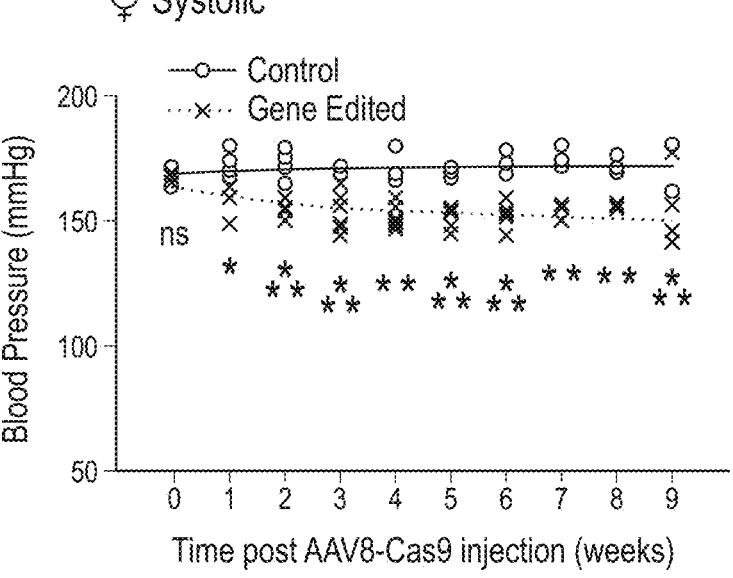
FIG. 7A, FIG. 7B, FIG. 7C, and FIG. 7D are line graphs showing that AGT gene editing reduces blood pressure in hypertensive SHR. AAV8-Cas9 (control) or AAV8-Cas9-AGTgRNA (gene-editing) viral particles ($2\times10^{12}$ viral particles) were injected into the tail vein of adult (12-week old) female (FIGS. 7A-B) and male (FIGS. 7C-D) SHR with established hypertension. Blood pressure measurements were made by tail-cuff for up to 9 weeks post-injection. N=4-5 per group. Ns not significant, *P<0.05, P<0.01, *P<0.001. The mean of the control and gene-edited groups is shown by the solid and dashed line respectively.
Figure 7B:
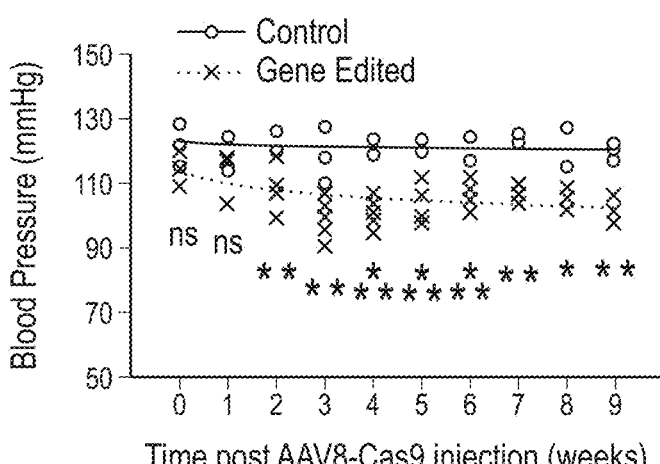
Figure 7C:
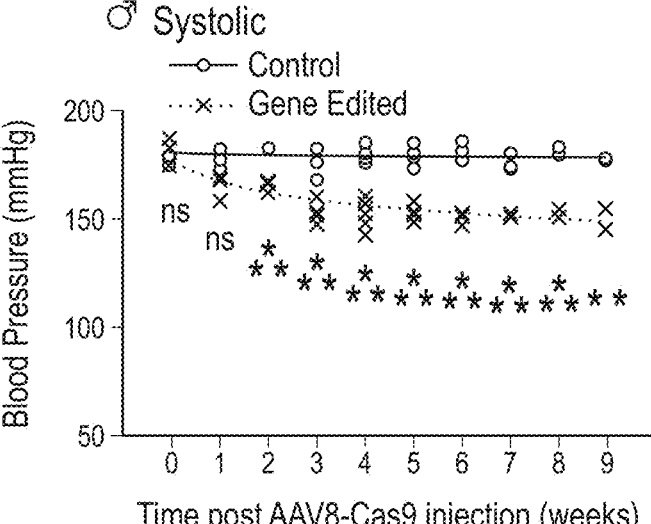
Figure 7D:
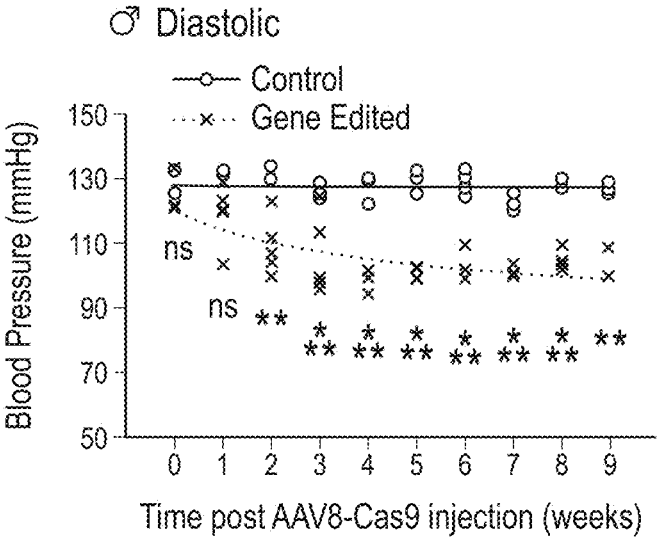

Following the demonstration that Crispr-Cas9 reduced AGT expression, the effect on blood pressure was measured. In control SHR, hypertension begins to be apparent around week 5 and progressively increased over time. Notably, injection of AAV8-Cas9-AGTgRNA particles into 5-week old SHR significantly prevented the progression of hypertension in these animals (FIGS. 6A-D). This effect was observed in both female and male SHR. Moreover, the effect was stronger on systolic versus diastolic blood pressure (FIGS. 6A-D). Importantly, the effects on hypertension were sustained as significant reductions in blood pressure were noted 1 year after injection of the AGT gene editing machinery (FIG. 6E).

Studies were carried out to determine whether AGT gene targeting would be effective in reducing blood pressure in adult SHR with established hypertension. In 12 week old SHR rats, hypertension was apparent and sustained (FIGS. 7A-D). Injection of AAV8-Cas9-AGTgRNA particles led to a rapid and progressive decrease in both systolic and diastolic blood pressure (FIGS. 7A-D). Blood pressure in AGT gene-edited SHR was comparable to WKY control rats. Importantly, the reductions in blood pressure were sustained for at least one year (FIGS. 7A-D).

Figure 8A:
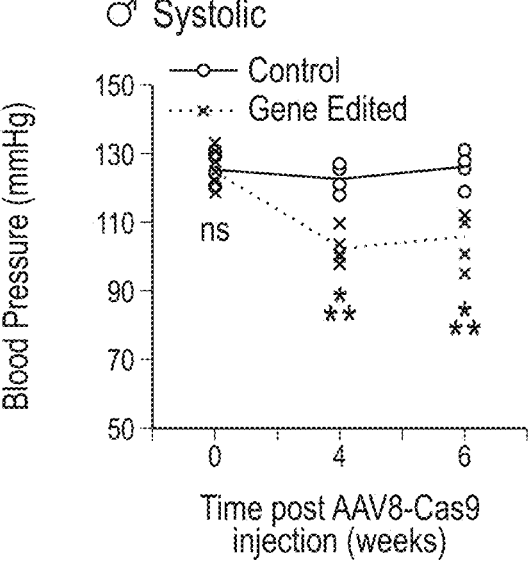
FIGS. 8A and 8B are line graphs showing that AGT gene-editing reduces blood pressure in WKY (control) rats. AAV8-Cas9-AGT gRNA was injected into the tail vein of adult (12-week old) of male WKY rats. Blood pressure measurements were made by tail-cuff 4- and 6-weeks post-injection. N=5 per group. N=5. P<0.01, *P<0.001. The mean of the control and gene-edited groups is shown by the solid and dashed line respectively.
Figure 8B:
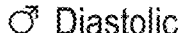
Figure 8B:
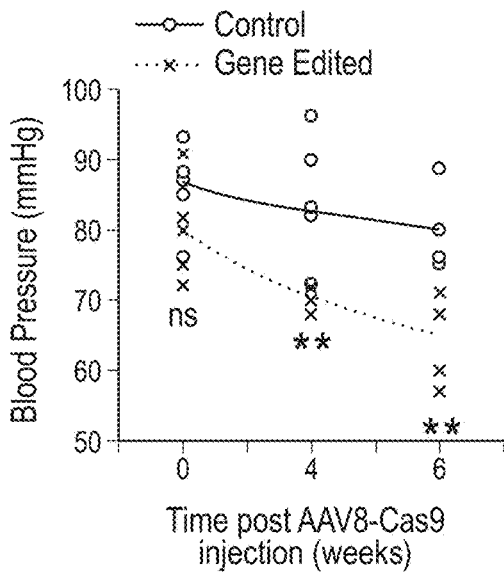

The control strain for the SHR rat model is the Wistar-Kyoto (WKY) strain. Both strains were derived from the outbred Wistar strain. In the WKY, gene editing of the AGT gene was similarly associated with prolonged reductions in both diastolic and systolic blood pressure (FIGS. 8A-B).

Figure 9A:
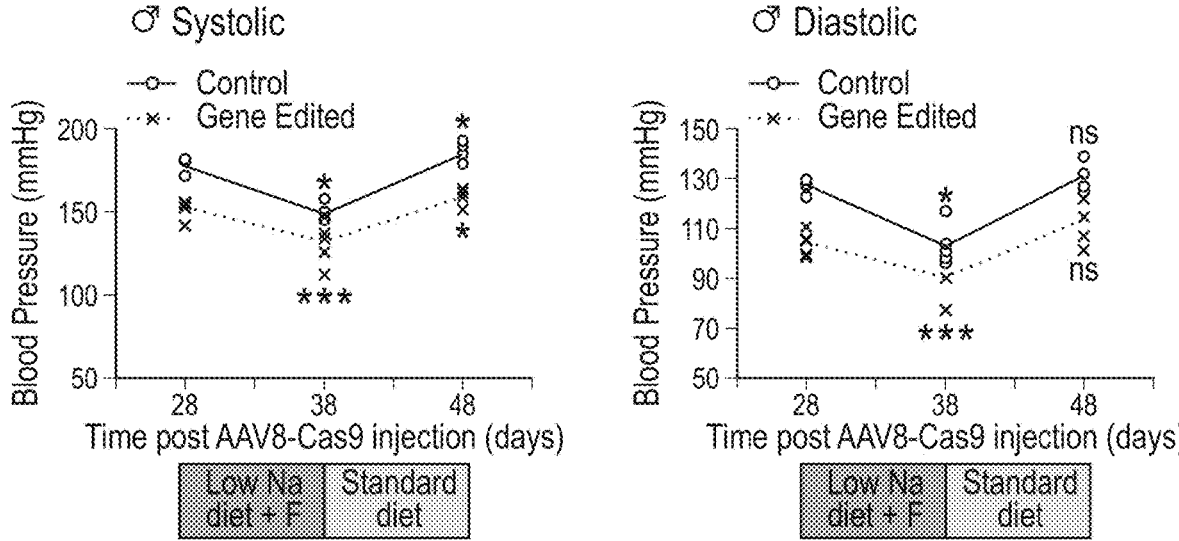
FIG. 9A is a series of line graphs shown systolic (left panel) and diastolic (right panel blood pressure post injection of AAV8-Cas9. Blood pressure measurements were made by tail-cuff at the indicated time-points.
Figures 9B, 9C:
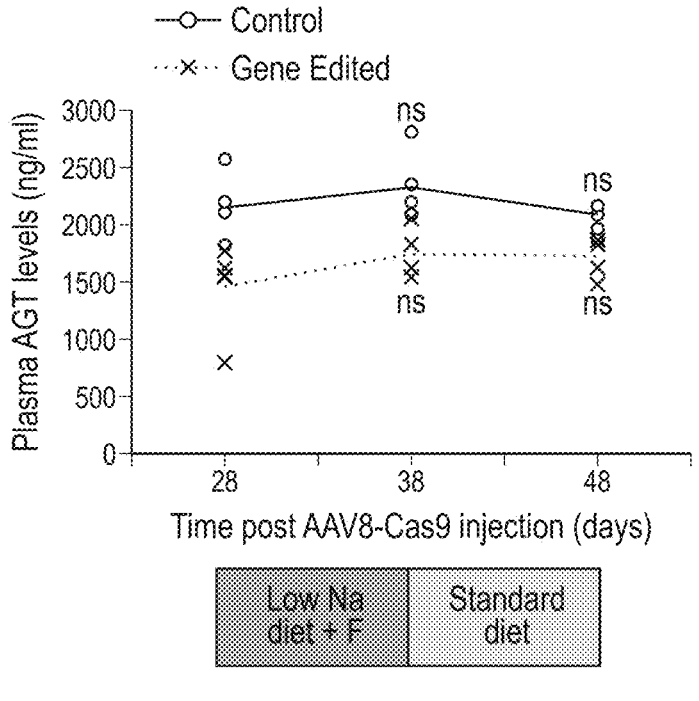
FIG. 9B is a line graph showing plasma AGT levels.
FIG. 9C is a line graph showing plasma AngI levels.
Figure 9D:
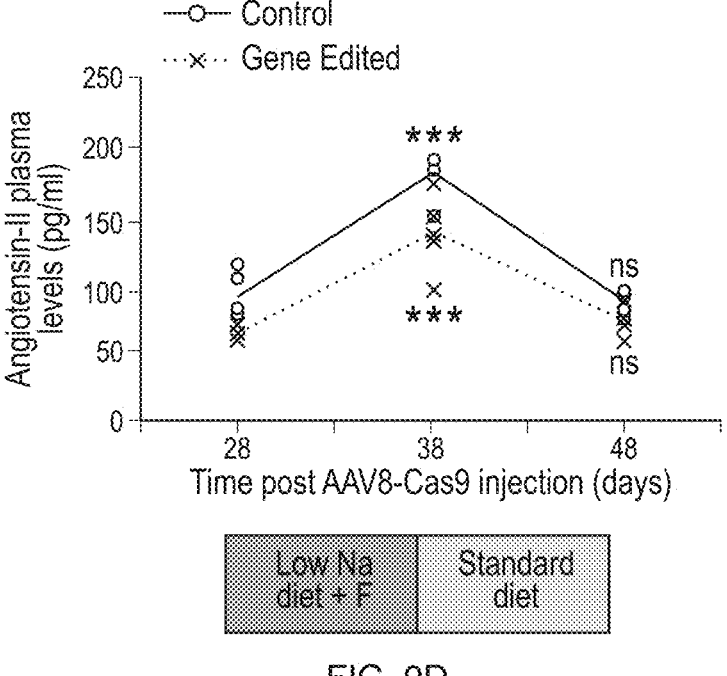
FIG. 9D is a line graph showing plasma AngII levels.
Figure 9E:
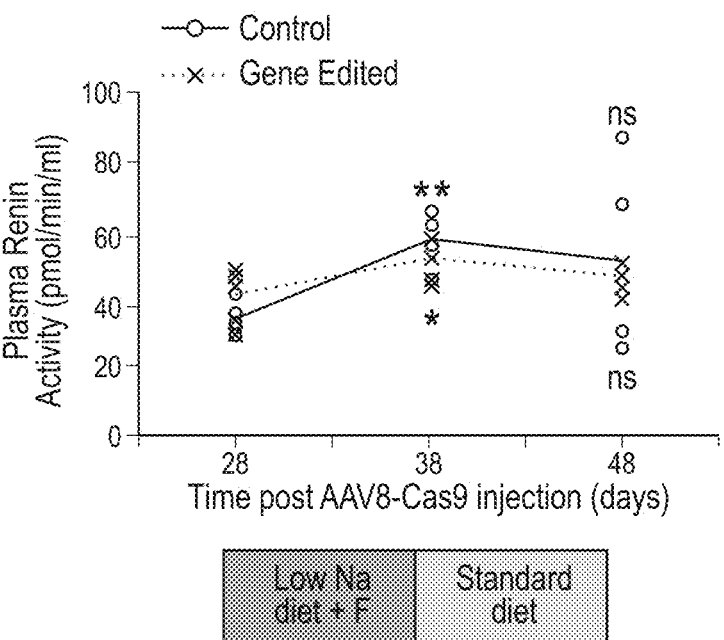
FIG. 9E is a line graph showing plasma Renin activity. In addition to blood pressure measurements, blood was taken from the animals by tail-vein and serum analyzed by ELISA for plasma (FIG. 9B) AGT levels.

Finally, the safety of AGT gene editing by studying the rats' ability to adapt to stress stimuli was examined using a low salt diet plus furosemide regimen. Adult SHR were injected with either control AAV8-Cas9 or AAV8-Cas9-AGTgRNA. Twenty-eight days after viral injection, by which point AGT gene editing had occurred, the SHR were placed on a low salt diet plus furosemide regimen for 10 days. Prior to starting the low salt diet plus furosemide regimen, systolic and diastolic blood pressures were significantly different between control and AGT gene-edited SHR (FIG. 9A, P<0.0001). In response to low salt diet plus furosemide regimen, blood pressures decreased in both SHR receiving the control AAV8-Cas9 and AGT gene-editing machinery. (FIG. 9A). The blood pressure in control SHR was 149±4/103±4 (mean±SEM) and for gene edited SHR was 132±6/91±4 mm Hg (P<0.05). Importantly, gene edited SHR did not develop hypotension. When the animals returned to their normal diet, blood pressure returned to baseline values for both groups (FIG. 9A). Once the animals had returned to baseline, blood pressure remained significantly lower in the AGT gene-edited group (FIG. 9A, P<0.0001). Plasma was analyzed for AGT, Angiotensin-I (Ang-I) and Angiotensin-II (Ang-II) levels; as well as renin activity. Low salt diet plus furosemide regimen resulted in significant increases in plasma renin activity in the control SHR associated with increases in plasma Ang-I and Ang-II levels but had no effect on plasma AGT levels (FIGS. 9B-E). The gene edited group exhibited similar responses. However, while the effects in the AGT gene-edited group were more attenuated, the values of AGT (P=0.005), Ang-I (P=0.025) and Ang-II (P=0.010) remained significantly reduced in the AGT-gene edited group. Importantly the plasma renin activity responses were not different between the 2 groups (P=0.424) (FIG. 5B-D). These data indicate that the gene editing regimen to control hypertension does not impair the normal physiological blood pressure response to dietary stimuli.

D. Long Term Control of Hypertension Using the Crispr-Cas9 System being Employed to Target RAAS The Crispr-Cas9 system has been employed to target RAAS for the effective control of hypertension. Moreover, the data described herein demonstrates that reducing AGT gene expression by gene editing has a direct effect on reducing blood pressure.

The gene-editing approach herein is distinctive from other approaches such as siRNA since Crispr-Cas9 system permanently disrupts the targeted gene without the need for continual expression of the Cas9 enzyme and repeated AAV administration or associated chronic effect on the immune system. Thus, Crispr-Cas9 mediated control of blood pressure is an important breakthrough for hypertension treatment and control.

An important demonstration of our study is the safety of AGT deletion using Crispr system. It was observed that the partial deletion of hepatic AGT gene, sufficient to control hypertension, did not block the renin angiotensin response to cardiovascular stress such as sodium depletion and furosemide. The data demonstrated that in response to sodium depletion and furosemide, the fall in blood pressure was protected by increased plasma renin activity with the associated generation of plasma angiotensin I and II in both control and Crispr treated SHRs. Indeed, the data showed that 40% ablation of hepatic AGT provided sufficient AGT as substrate for increased plasma renin to generate plasma angiotensin comparable to control SHR. Beyond the effects of gene-editing hepatic AGT, one major safety concern with Crispr-Cas9 mediated gene-editing is the potential for off target events. Off-target events, defined as events at unintended genomic sequences, are relatively rare. However, while rare, the possibility of random alterations to the genome has spurred further development of the gene-editing toolkit. In this regard, modification of the DNA nuclease has been an important area of focus with substitutions of Cas9 with alternative nucleases such as Cpf-1 and Fok-1 further reducing the rate of random mutations. AAV8 was chosen to deliver the gene-editing machinery specifically to the liver, because AAV8 is known to specifically target the liver. As such, an extrahepatic effect has not been observed (based on many published studies that AAV8 delivery of transgenes have no other tissue effects). Thus, an advantage of the methods described herein is the safety profile (few or no off-target effects) for use to treat human hypertension.

39

TABLE 2

| AAV Serotypes and Their Respective Tropism | | | | | | | | |
|---|---|---|---|---|---|---|---|---|
| AAV Serotype | Tissue tropism | | | | | | | |
| | CNS | Retina | Lung | Liver | Pancreas | Kidney | Heart | Muscle |
| AAV1 | X | X | | | X | | X | X |
| AAV2 | | X | | X | | X | | |
| AAV3 | | X | X | X | | | X | |
| AAV4 | X | X | | | | | X | |
| AAV5 | X | X | X | | X | | | |
| AAV6 | X | | X | X | | | X | X |
| AAV7 | | | | X | | | | X |
| AAV8 | | X | | X | X | | | X |
| AAV9 | X | | X | X | | | X | X |
| AAV-DJ | | X | X | X | | X | | |
| AAV-DJ/8 | | X | | X | | | | X |
| AAV-Rh10 | X | | X | X | | | X | X |
| AAV-retro | X | X | | | | | | X |
| AAV-PHP.B | X | | | | | | X | X |
| AAV8-PHP.eB | X | | | | | | | X |
| AAV-PHP.S | X | | | | | | X | X |

A limited number of studies have shown that targeting of other genes via the Crispr-Cas9 system resulted in variable and modest effect of blood pressure. Yang et al utilized the Crispr-Cas9 system to ablate the CPI-17 gene as well as to prevent the activation of the CPI-17 protein by preventing the phosphorylation of a key residue. In both models, mean blood pressure was reduced by between 3 and 6 mmHg. The reduction in blood pressure was found to be associated with reduced blood vessel contractility. Another study demonstrated that Crispr-Cas9 mediated ablation of Gper (G protein coupled estrogen receptor) reduced blood pressure in the SHR model by affecting the gut microbiome. Indeed, the authors were able to reverse the reductions in blood pressure by transplanting the gut microbiota from a wild-type SHR into the gut of the Gper knockout animals. This may explain why previous Gper gene ablation models have shown both increased and decreased blood pressure measurements.

The data described herein demonstrate that targeting RAAS with the Crispr-Cas9 system is an effective method for achieving a safe, sustainable reduction in blood pressure that is useful for life-long control of hypertension. Over the years, there have been significant efforts in finding a method of lifelong control and possibly cure for hypertension, such as the development of a vaccine, but without success. Crispr-AAV8 is a technology that can be delivered systemically as somatic therapy at any age, thereby fulfilling a longfelt unmet need in the field.

OTHER EMBODIMENTS

One skilled in the art will readily appreciate that the present disclosure is well adapted to carry out the objects and obtain the ends and advantages mentioned, as well as those inherent therein. The present disclosure described herein are presently representative of preferred embodiments, are exemplary, and are not intended as limitations on the scope of the present disclosure. Changes therein and other uses will occur to those skilled in the art which are encompassed within the spirit of the present disclosure as defined by the scope of the claims.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

Representative claims are provided below. These claims are representative in nature of at least some aspects of the subject matter disclosed in this provisional patent application. These claims are not meant to limit the scope of the subject matter disclosed herein, but are provided for representative purposes only.

SEQUENCE LISTING

```
Sequence total quantity: 29
SEQ ID NO: 1          moltype = DNA  length = 21
FEATURE               Location/Qualifiers
misc_feature          1..21
                      note = Description of Artificial Sequence: Synthetic
                      oligonucleotide
source                1..21
                      mol_type = other DNA
                      organism = synthetic construct
SEQUENCE: 1
ccttccacct cgtcatccac a                                          21

SEQ ID NO: 2          moltype = DNA  length = 21
FEATURE               Location/Qualifiers
misc_feature          1..21
                      note = Description of Artificial Sequence: Synthetic
                      oligonucleotide
source                1..21
                      mol_type = other DNA
                      organism = synthetic construct
SEQUENCE: 2
tcattgtgga tgacgaggtg g                                          21
```

```
SEQ ID NO: 3            moltype = DNA   length = 21
FEATURE                 Location/Qualifiers
misc_feature            1..21
                        note = Description of Artificial Sequence: Synthetic
                         oligonucleotide
source                  1..21
                        mol_type = other DNA
                        organism = synthetic construct
SEQUENCE: 3
gatatttcag ggtatgcgga a                                              21

SEQ ID NO: 4            moltype = AA   length = 10
FEATURE                 Location/Qualifiers
REGION                  1..10
                        note = Description of Unknown: target region sequence
source                  1..10
                        mol_type = protein
                        organism = unidentified
SEQUENCE: 4
DRVYIHPFHL                                                           10

SEQ ID NO: 5            moltype = DNA   length = 1431
FEATURE                 Location/Qualifiers
source                  1..1431
                        mol_type = other DNA
                        organism = Homo sapiens
SEQUENCE: 5
atggctcctg ccggtgtgag cctgagggcc accatcctct gcctcctggc ctgggctggc   60
ctggctgcag gtgaccgggt gtacatacac cccttccacc tcgtcatcca caatgagagt   120
acctgtgagc agctggcaaa ggccaatgcc gggaagccca aagaccccac cttcatacct   180
gctccaattc aggccaagac atccctgtg gatgaaaagg ccctacagga ccagctggtg   240
ctagtcgctg caaaacttga caccgaagac aagttgaggg ccgcaatggt cgggatgctg   300
gccaacttct tgggcttccg tatatatggc atgcacagtg agctatgggg cgtggtccat   360
ggggccaccg tcctctcccc aacggctgtc tttggcaccc tggcctctct ctatctggga   420
gccttggacc acacagctga caggctacag gcaatcctgg gtgttccttg gaaggacaag   480
aactgcacct cccggctgga tgcgcacaag gtcctgtctg ccctgcaggc tgtacagggc   540
ctgctagtgg cccagggcag ggctgatagc caggcccagc tgctgctgtc cacggtggtg   600
ggcgtgttca gcccccagg cctgcacctg aagcagccgt ttgtgcaggg cctggctctc   660
tataccctg tggtcctccc acgctctctg gacttcacag aactggatgt tgctgctgag   720
aagattgaca ggttcatgca ggctgtgaca ggatggaaga ctggctgctc cctgatggga   780
gccagtgtgg acagcaccct ggctttcaac acctacgtcc acttccaagg gaagatgaag   840
ggcttctccc tgctggccga gccccaggag ttctgggtgg acaacagcac ctcagtgtct   900
gttcccatgc tctctggcat gggcaccttc cagcactgga gtgacatcca ggacaacttc   960
tcggtgactc aagtgccctt cactgagagc gcctgcctgc tgctgatcca gcctcactat   1020
gcctctgacc tggacaaggt ggagggtctc actttccagc aaaactccct caactggatg   1080
aagaaactat ctccccggac catccacctg accatgcccc aactggtgct gcaaggatct   1140
tatgacctgc aggacctgct cgcccaggct gagctgcccg ccattctgca caccgagctg   1200
aacctgcaaa aattgagcaa tgaccgcatc agggtgggg aggtgctgaa cagcattttt   1260
tttgagcttg aagcggatga gagagagccc acagagtcta cccaacagct taacaagcct   1320
gaggtcttga aggtgaccct gaaccgccca ttcctgtttg ctgtgtatga tcaaagcgcc   1380
actgccctgc acttcctggg ccgcgtggcc aacccgctga gcacacagatg a          1431

SEQ ID NO: 6            moltype = AA   length = 485
FEATURE                 Location/Qualifiers
source                  1..485
                        mol_type = protein
                        organism = Homo sapiens
SEQUENCE: 6
MRKRAPQSEM APAGVSLRAT ILCLLAWAGL AAGDRVYIHP FHLVIHNEST CEQLAKANAG   60
KPKDPTFIPA PIQAKTSPVD EKALQDQLVL VAAKLDTEDK LRAAMVGMLA NFLGFRIYGM   120
HSELWGVVHG ATVLSPTAVF GTLASLYLGA LDHTADRLQA ILGVPWKDKN CTSRLDAHKV   180
LSALQAVQGL LVAQGRADSQ AQLLLSTVVG VFTAPGLHLK QPFVQGLALY TPVVLPRSLD   240
FTELDVAAEK IDRFMQAVTG WKTGCSLMGA SVDSTLAFNT YVHFQGKMKG FSLLAEPQEF   300
WVDNSTSVSV PMLSGMGTFQ HWSDIQDNFS VTQVPFTESA CLLLIQPHYA SDLDKVEGLT   360
FQQNSLNWMK KLSPRTIHLT MPQLVLQGSY DLQDLLAQAE LPAILHTELN LQKLSNDRIR   420
VGEVLNSIFF ELEADEREPT ESTQQLNKPE VLEVTLNRPF LFAVYDQSAT ALHFLGRVAN   480
PLSTA                                                               485

SEQ ID NO: 7            moltype = DNA   length = 1434
FEATURE                 Location/Qualifiers
source                  1..1434
                        mol_type = other DNA
                        organism = Rattus sp.
SEQUENCE: 7
atgactccca cggggggcagg cctgaaggcc accatcttct gcatcctgac ctgggtcagc   60
ctgacagctg gggaccgcgt atacatccac cccttcatc tcctctacta cagcaagagc   120
acctgcgccc agctggagaa ccccagtgtg gagacgctcc cagagccaac ctttgagcct   180
gtgcccattc aggccaagac ctccccgtg gatgagaaga ccctgcgaga taagctcgtg   240
ctggccactg agaagctaga ggctgaggat cggcagcgag ctgcccaggt cgcgatgatt   300
```

```
gccaacttca tgggtttccg catgtacaag atgctgagtg aggcaagagg tgtagccagt   360
ggggccgtcc tctctccacc ggccctcttt ggcaccctgg tctctttcta ccttggatcg   420
ttggatccca cggccagcca gttgcaggtg ctgctgggcg tccctgtgaa ggagggagac   480
tgcacctccc ggctggacgg acataaggtc ctcactgccc tgcaggctgt tcagggcttg   540
ctggtcaccc agggtggaag cagcagccag acacccctgc tacagtccac cgtggtgggc   600
ctcttcactg ccccaggctt gcgcctaaaa cagccatttg ttgagagctt gggtcccttc   660
accccgcca tcttccctcg ctctctggac ttatccactg acccagttct tgctgcccag   720
aaaatcaaca ggtttgtgca ggctgtgaca gggtggaaga tgaacttgcc actagagggg   780
gtcagcacgg acagcaccct atttttcaac acctacgttc acttccaagg gaagatgaga   840
ggcttctccc agctgactgg gctccatgag ttctgggtgg acaacagcac ctcagtgtct   900
gtgcccatgc tctcgggcac tggcaacttc cagcactgga gtgacgccca gaacaacttc   960
tccgtgacac gcgtgcccct gggtgagagt gtcaccctgc tgctgatcca gccccagtgc  1020
gcctcagatc tcgacagggt ggaggtcctc gtcttccagc acgacttcct gacttggata  1080
aagaaccgc ctcctcgggc catccgtctg accctgccgc agctggaaat tcggggatcc  1140
tacaacctgc aggacctgct ggctcaggcc aagctgtcta ccctttttggg tgctgaggca  1200
aatctgggca agatgggtga caccaacccc cgagtgggag aggttctcaa cagcatcctc  1260
cttgaactcc aagcaggcga ggaggagcag cccacagagt ctgcccagca gcctggctca  1320
cccgaggtgc tggacgtgac cctgagcagt ccgttcctgt tcgccatcta cgagcgggac  1380
tcaggtgcgc tgcactttct gggcagagtg gataacccc aaaatgtggt gtga         1434

SEQ ID NO: 8            moltype = AA   length = 477
FEATURE                 Location/Qualifiers
source                  1..477
                        mol_type = protein
                        organism = Rattus sp.
SEQUENCE: 8
MTPTGAGLKA TIFCILTWVS LTAGDRVYIH PFHLLYYSKS TCAQLENPSV ETLPEPTFEP   60
VPIQAKTSPV DEKTLRDKLV LATEKLEAED RQRAAQVAMI ANFMGFRMYK MLSEARGVAS  120
GAVLSPPALF GTLVSFYLGS LDPTASQLQV LLGVPVKEGD CTSRLDGHKV LTALQAVQGL  180
LVTQGGSSSQ TPLLQSTVVG LFTAPGLRLK QPFVESLGPF TPAIFPRSLD LSTDPVLAAQ  240
KINRFVQAVT GWKMNLPLEG VSTDSTLFFN TYVHFQGKMR GFSQLTGLHE FWVDNSTSVS  300
VPMLSGTGNF QHWSDAQNNF SVTRVPLGES VTLLLIQPQC ASDLDRVEVL VPQHDFLTWI  360
KNPPPRAIRL TLPQLEIRGS YNLQDLLAQA KLSTLLGAEA NLGKMGDTNP RVGEVLNSIL  420
LELQAGEEEQ PTESAQQPGS PEVLDVTLSS PFLFAIYERD SGALHFLGRV DNPQNVV     477

SEQ ID NO: 9            moltype = DNA   length = 26
FEATURE                 Location/Qualifiers
misc_feature            1..26
                        note = Description of Artificial Sequence: Synthetic primer
source                  1..26
                        mol_type = other DNA
                        organism = synthetic construct
SEQUENCE: 9
caccgtgctg tagtagagga gatgaa                                          26

SEQ ID NO: 10           moltype = DNA   length = 26
FEATURE                 Location/Qualifiers
misc_feature            1..26
                        note = Description of Artificial Sequence: Synthetic primer
source                  1..26
                        mol_type = other DNA
                        organism = synthetic construct
SEQUENCE: 10
aaacttcatc tcctctacta cagcac                                          26

SEQ ID NO: 11           moltype = DNA   length = 21
FEATURE                 Location/Qualifiers
misc_feature            1..21
                        note = Description of Artificial Sequence: Synthetic
                         oligonucleotide
source                  1..21
                        mol_type = other DNA
                        organism = synthetic construct
SEQUENCE: 11
tgctgtagta gaggagatga a                                               21

SEQ ID NO: 12           moltype = DNA   length = 25
FEATURE                 Location/Qualifiers
misc_feature            1..25
                        note = Description of Artificial Sequence: Synthetic primer
source                  1..25
                        mol_type = other DNA
                        organism = synthetic construct
SEQUENCE: 12
caccggtctg gctgctgctt ccacc                                           25

SEQ ID NO: 13           moltype = DNA   length = 25
FEATURE                 Location/Qualifiers
misc_feature            1..25
```

-continued

```
                        note = Description of Artificial Sequence: Synthetic primer
source                  1..25
                        mol_type = other DNA
                        organism = synthetic construct
SEQUENCE: 13
aaacggtgga agcagcagcc agacc                                        25

SEQ ID NO: 14           moltype = DNA  length = 25
FEATURE                 Location/Qualifiers
misc_feature            1..25
                        note = Description of Artificial Sequence: Synthetic primer
source                  1..25
                        mol_type = other DNA
                        organism = synthetic construct
SEQUENCE: 14
caccgtagta gaggagatga aaggg                                        25

SEQ ID NO: 15           moltype = DNA  length = 25
FEATURE                 Location/Qualifiers
misc_feature            1..25
                        note = Description of Artificial Sequence: Synthetic primer
source                  1..25
                        mol_type = other DNA
                        organism = synthetic construct
SEQUENCE: 15
aaaccccttt catctcctct actac                                        25

SEQ ID NO: 16           moltype = DNA  length = 22
FEATURE                 Location/Qualifiers
misc_feature            1..22
                        note = Description of Artificial Sequence: Synthetic primer
source                  1..22
                        mol_type = other DNA
                        organism = synthetic construct
SEQUENCE: 16
aagcaagtcc acagatccgt ga                                           22

SEQ ID NO: 17           moltype = DNA  length = 22
FEATURE                 Location/Qualifiers
misc_feature            1..22
                        note = Description of Artificial Sequence: Synthetic primer
source                  1..22
                        mol_type = other DNA
                        organism = synthetic construct
SEQUENCE: 17
ctctgtccct ctcacgcatg aa                                           22

SEQ ID NO: 18           moltype = DNA  length = 21
FEATURE                 Location/Qualifiers
misc_feature            1..21
                        note = Description of Artificial Sequence: Synthetic primer
source                  1..21
                        mol_type = other DNA
                        organism = synthetic construct
SEQUENCE: 18
ggaacccta gtgatggagt t                                             21

SEQ ID NO: 19           moltype = DNA  length = 16
FEATURE                 Location/Qualifiers
misc_feature            1..16
                        note = Description of Artificial Sequence: Synthetic primer
source                  1..16
                        mol_type = other DNA
                        organism = synthetic construct
SEQUENCE: 19
cggcctcagt gagcga                                                  16

SEQ ID NO: 20           moltype = DNA  length = 26
FEATURE                 Location/Qualifiers
misc_feature            1..26
                        note = Description of Artificial Sequence: Synthetic primer
source                  1..26
                        mol_type = other DNA
                        organism = synthetic construct
SEQUENCE: 20
caccgccttc cacctcgtca tccaca                                       26

SEQ ID NO: 21           moltype = DNA  length = 26
FEATURE                 Location/Qualifiers
```

```
misc_feature           1..26
                       note = Description of Artificial Sequence: Synthetic primer
source                 1..26
                       mol_type = other DNA
                       organism = synthetic construct
SEQUENCE: 21
aaactgtgga tgacgaggtg gaaggc                                            26

SEQ ID NO: 22          moltype = DNA  length = 26
FEATURE                Location/Qualifiers
misc_feature           1..26
                       note = Description of Artificial Sequence: Synthetic primer
source                 1..26
                       mol_type = other DNA
                       organism = synthetic construct
SEQUENCE: 22
caccgtcatt gtggatgacg aggtgg                                            26

SEQ ID NO: 23          moltype = DNA  length = 26
FEATURE                Location/Qualifiers
misc_feature           1..26
                       note = Description of Artificial Sequence: Synthetic primer
source                 1..26
                       mol_type = other DNA
                       organism = synthetic construct
SEQUENCE: 23
aaacccacct cgtcatccac aatgac                                            26

SEQ ID NO: 24          moltype = DNA  length = 25
FEATURE                Location/Qualifiers
misc_feature           1..25
                       note = Description of Artificial Sequence: Synthetic primer
source                 1..25
                       mol_type = other DNA
                       organism = synthetic construct
SEQUENCE: 24
caccgatatt tcagggtatg cggaa                                             25

SEQ ID NO: 25          moltype = DNA  length = 25
FEATURE                Location/Qualifiers
misc_feature           1..25
                       note = Description of Artificial Sequence: Synthetic primer
source                 1..25
                       mol_type = other DNA
                       organism = synthetic construct
SEQUENCE: 25
aaacttccgc ataccctgaa atatc                                             25

SEQ ID NO: 26          moltype = AA  length = 18
FEATURE                Location/Qualifiers
REGION                 1..18
                       note = Description of Unknown: AGT sequence
source                 1..18
                       mol_type = protein
                       organism = unidentified
SEQUENCE: 26
DRVYIHPFHL VIHDESTC                                                     18

SEQ ID NO: 27          moltype = DNA  length = 23
FEATURE                Location/Qualifiers
misc_feature           1..23
                       note = Description of Unknown: AGT exon 2 sequence
source                 1..23
                       mol_type = other DNA
                       organism = unidentified
SEQUENCE: 27
cacagaagca agtccacaga tcc                                               23

SEQ ID NO: 28          moltype = DNA  length = 23
FEATURE                Location/Qualifiers
misc_feature           1..23
                       note = Description of Unknown: AGT exon 2 sequence
source                 1..23
                       mol_type = other DNA
                       organism = unidentified
SEQUENCE: 28
ccacgggggc aggcctgaag gcc                                               23

SEQ ID NO: 29          moltype = AA  length = 7
```

-continued

```
FEATURE          Location/Qualifiers
REGION           1..7
                 note = Description of Unknown: AGT exon 2 sequence
source           1..7
                 mol_type = protein
                 organism = unidentified
SEQUENCE: 29
TGAGLKA                                                          7
```

What is claimed:

1. A guide RNA (gRNA) that targets an angiotensinogen (AGT) gene and comprising the polynucleotide sequence of guide RNA to target human AGT gene comprises CCTTC-CACCTCGTCATCCACA (human gRNA1; SEQ ID NO: 1); TCATTGTGGATGACGAGGTGG (human gRNA2; SEQ ID NO:2), or GATATTTCAGGGTATGCGGAA (human gRNA3; SEQ ID NO:3).

2. The gRNA of claim 1, further comprising a hepatocyte-tropic vector.

3. The gRNA of claim 2, wherein the vector comprises adeno-associated virus-8 (AAV-8).

4. The gRNA of claim 1, further comprising a heart-tropic vector, a neuronal cell-tropic vector, or a kidney-tropic vector.

5. The gRNA of claim 4, wherein the heart-tropic vector comprises AAV-1 or AAV-9, the neuronal cell-tropic vector comprises AAV-1, AAV-4, AAV-5, or AAV-6, and the kidney-tropic vector comprises AAV-2 or AAV-DJ.

6. The gRNA of claim 1, further comprising a CRISPR/Cas system component, wherein the component comprises at least a Cas9 nuclease.

7. A method of treating a subject suffering from hypertension or prehypertension, comprising administering to the subject a composition comprising; (i) a guide RNA (gRNA) that targets an angiotensinogen (AGT) gene, said gRNA comprising the polynucleotide sequence of CCTTC-CACCTCGTCATCCACA (human gRNA1; SEQ ID NO:1); TCATTGTGGATGACGAGGTGG (human gRNA2; SEQ ID NO:2), or GATATTTCAGGGTATGCGGAA (human gRNA3; SEQ ID NO:3); (ii) a hepatocyte-tropic vector; and (iii) a CRISPR/Cas system comprising a Cas9 nuclease.

8. The method of claim 7, wherein the hepatocyte-tropic vector comprises AAV-1, AAV-2, AAV-4, AAV-5, AAV-6, AAV-8, AAV-9 or AAV-DJ.

9. The method of claim 7, wherein the AGT gene comprises an AGT-II gene.

10. The method of claim 7 wherein the AGT gene is deleted in a cell comprising the administered composition.

11. The method of claim 7, wherein systolic or diastolic blood pressure is reduced by at least 10 millimeters of mercury (mm Hg).

12. The method of claim 7, wherein the composition is administered intravenously.

13. The method of claim 7, wherein the composition is administered to a human subject at a dose of about $1\text{-}2\times10^{15}$ genome copies of AAV per 60 kg.

14. The method of claim 7, wherein the composition is administered once in the subject's life time.

15. The method of claim 7, wherein the composition is administered annually.

16. The method of claim 7, wherein the composition is administered every 2-5 years.

17. A DNA targeting composition or vector comprising an endonuclease and at least one gRNA of claim 1.

18. A kit comprising a DNA targeting composition or vector comprising a Cas9 nuclease and at least one gRNA of claim 1 and instructions for use to reduce blood pressure in a mammalian subject.

* * * * *